United States Patent
Wade et al.

(12)

(10) Patent No.: US 6,455,252 B1
(45) Date of Patent: *Sep. 24, 2002

(54) DETERMINATION OF GENETIC SEX IN EQUINE SPECIES BY ANALYSIS OF Y-CHROMOSOMAL DNA SEQUENCES

(75) Inventors: Nicholas Michael Wade; Bruce Thomas Harrison; Brian William King; Kenneth Clifford Reed; Kathleen Margaret Murphy, all of Queensland (AU)

(73) Assignee: Wu Li Dance Company Pty Ltd., Queensland (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/462,561

(22) PCT Filed: Jul. 9, 1998

(86) PCT No.: PCT/AU98/00533

§ 371 (c)(1),
(2), (4) Date: Mar. 22, 2000

(87) PCT Pub. No.: WO99/02672

PCT Pub. Date: Jan. 21, 1999

(30) Foreign Application Priority Data

Jul. 9, 1997 (AU) ............................................. PO 7802

(51) Int. Cl.$^7$ .......................... C07H 21/04; C12Q 1/68; C12P 19/34
(52) U.S. Cl. ...................... 435/6; 435/91.2; 536/24.31; 536/24.3; 536/23.1
(58) Field of Search ................. 435/6, 91.2; 536/24.31, 536/24.3

(56) References Cited

PUBLICATIONS

Djikeng et al. GenBank Accession No. AA1862412. Jan. 1997.*
El–Sayed. GenBank Accession No. T26234. Nov. 1995.*
Matthew. Methods in Molecular Biology, Humana Press, John M. Walker, ed. 1994, p. 257–261.*
Stratagene Cataolog. 1998. p. 39.*

* cited by examiner

*Primary Examiner*—Jeffrey Fredman
*Assistant Examiner*—Juliet C. Einsmann
(74) *Attorney, Agent, or Firm*—Nixon & Vanderhye

(57) ABSTRACT

The present invention relates to DNA sequences, probes and primers specific to the Y chromosome of *Equus caballus*. The present invention also relates to methods of determining the sex of a horse, a equine fetus, and equine embryo or equine cells. The present invention further relates to a method for the isolation of Y-chromosomal DNA sequences.

22 Claims, 10 Drawing Sheets

FIG. 2

```
              10        20        30        40        50
Cloned: 5'-GTCGTAGCGGAGAAAGGAATCTCTGGATTCCATGCAATCCCAGTCAAAGT
Male:      5'-GTAGCGGAGAAAGGAATCTCTGGATTCCATGCAATCCCAGTCAAAGT
Female:      5'-KCGGAGGGAGGAATGTATGTATTGCATGCAATCCCAGTCAAAGT
                 .   ..      . . . . .
              60        70        80        90       100
        GGCAGCCATATTTGCCGGAGAGATAGAAGAGAGAATCCTAAAGTGTCTAG
        GGCAGCCATATTTGCCAGAGAGATAGAAGAGAGAATCCTAAAGTTTCTAG
        GGCAGCCATATTTGCCAGAGAGATAGAAGAGAGAATCCTAAAGTTTCTAG
                         *                         *
             110       120       130       140       150
        CCAGCAACAAGAGCCCCTGAATAGGCCAAGGAATCCTCAGGAAAACGAAC
        CCAGCAACAAGAGCCCCTGAATAGGCCAAGGAATCCTCAGGAAAACGAAC
        CCAGCAACAAGAGCCCCTGAATAGGCCAAGGAATCCTCAGGAAAACGAAC 160       170       180       190       200
        AAAGCAGGACGGATCACACTTTCTGATTTCAACATAGAGGACGAAGCGCT
        AAAGCAGGACGTATCACACTTTCTGATTTCAACATAGAGGACGAAGCGCT
        AAAGCAGGACGTATCACACTTTCTGATTTCAACCTAAAGGACCACKCGGT
                   *                      .  ..  .  ... .
             210       220       230
        AGGTACCGAAACGGAACAGTCCGCTACGAC-3'
        AGGTACCGAAACGGAACAGTCGC-3'
        AGGTACCGAGACGGATCGTCCGC-3'
                 .   . ...  **
```

FIG. 3A
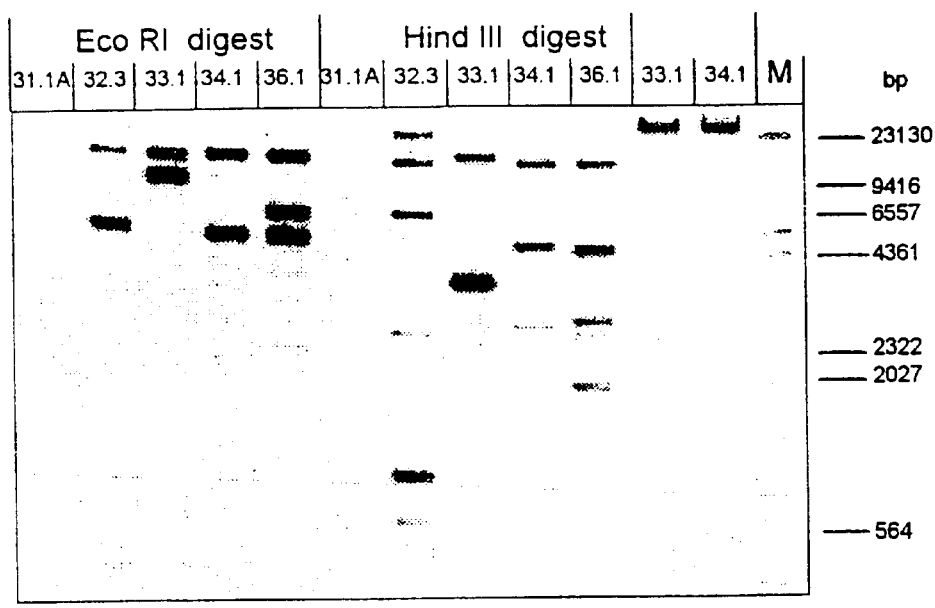
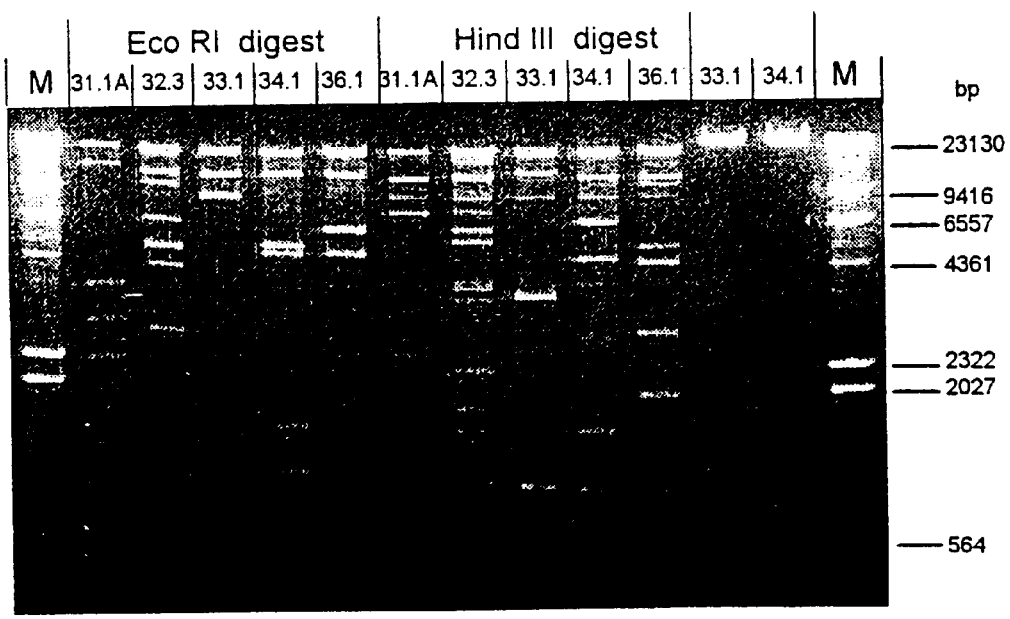

FIG. 3B
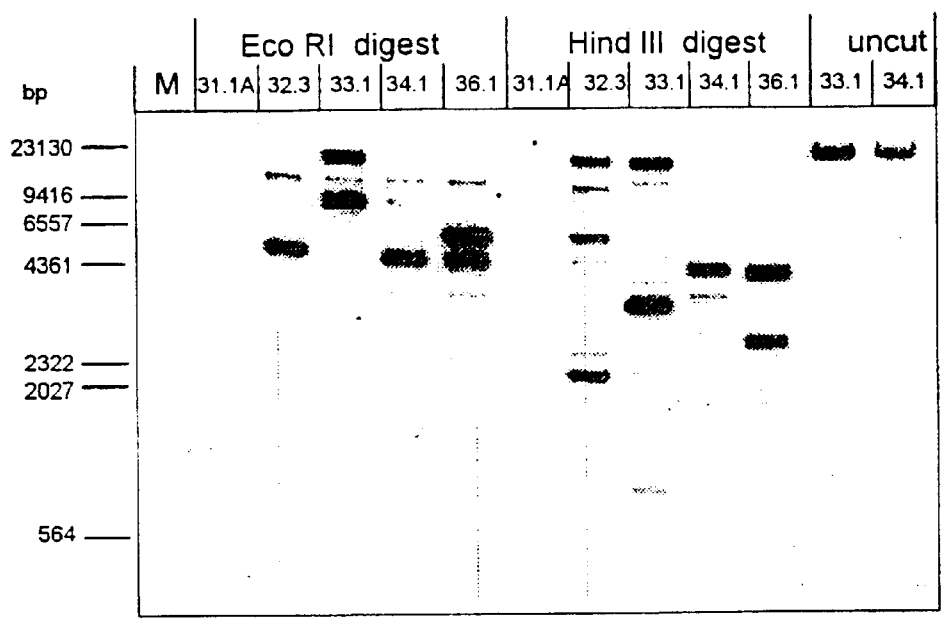
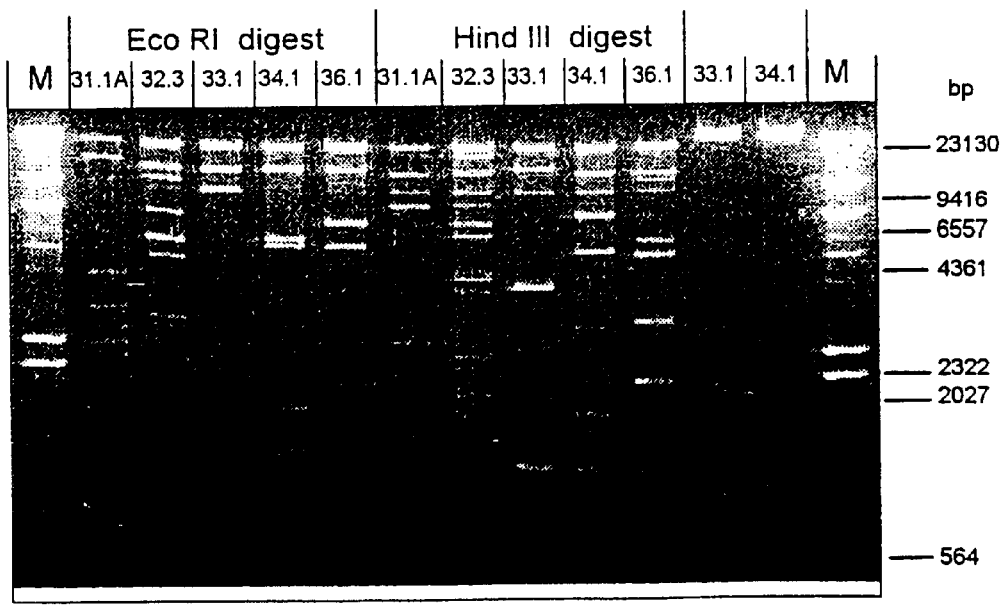

DETERMINATION OF GENETIC SEX IN EQUINE SPECIES BY ANALYSIS OF Y-CHROMOSOMAL DNA SEQUENCES

FIELD OF THE INVENTION

The present invention relates to polynucleotide sequences associated with the equine Y chromosome and to methods of identifying such polynucleotide sequences. The present invention also relates to methods of determining the primary (i.e. genetic) sex of individuals and of samples of cells removed from individuals, and is particularly concerned with equine sex determination.

BACKGROUND OF THE INVENTION

Many sectors of the various horse industries prefer a preponderance of animals of one sex. This may be for reasons of reproductive potential, heritability of particular traits, tractability, performance, stature and physique, appearance or other reasons.

The ability to determine the sex of a fetus is advantageous since it allows optimal management and valuation of pregnancies.

Where methods of assisted reproduction are available, by embryo transfer (with or without induced multiple ovulation) or by recovers and return into the donor or by in vitro fertilisation, the ability to determine the sex of an embryo is advantageous since it allows the sex of potential progeny to be predetermined. If combined with artificial twinning by means of embryo bisection (1,2) it further allows enhanced propagation of the desired sex without reduction in the total number of potential progeny.

It would be particularly advantageous to predetermine the sex of progeny by means of insemination of a receptive mare with sperm populations comprising a preponderance of sperm having one or the other sex chromosome constitution, i.e. either the X chromosome (which sperm yield female progeny) or the Y chromosome (which sperm yield male progeny). Such enriched populations of sperm could also be used to great advantage in in vitro fertilisation. In a further very advantageous application, an individual sperm cell of a known sex chromosome constitution can be injected into the cytoplasm of a mature oocyte in vitro (ICSI: intracytoplasmic sperm injection), effecting fertilisation to yield a zygote of known sex. The ability to determine the sex chromosome constitution of populations of sperm cells and of individual sperm cells is an essential prerequisite in such applications.

The primary sex of equine species, as in the overwhelming majority of mammalian species, is determined by the presence or absence of the entire Y chromosome or a functional portion thereof (3–8). The essential portion is a gene known as SRY that is responsible for initiating testis differentiation (9–11). Secretions of the resultant testis have a dominant influence on the development of secondary sex characters (12).

The sex or presumptive sex of an individual horse can thus be determined by analysis for DNA sequences that are associated uniquely with the equine Y chromosome.

Previous reports of DNA sequences associated with the equine Y chromosome (11,13,14) concern presumptive sequences that are amplified by polymerase chain reaction (PCR; 15,16) from primer oligonucleotides whose sequences are derived from genes known to be Y-linked in other mammalian species, viz. ZFY(13,14) and SRY(11,13). There are no published DNA sequence data for DNA sequences associated with the equine Y chromosome. Both ZFY and SRY occur in single copy in all mammalian species examined (with the known exception of Mus species, in which two similar Zfv genes have been described; 17) and so, presumably, in the horse. In the context of determining the genetic sex of viable embryos where only a small number of cells is available from a microscopic biopsy, assay sensitivity is a significant consideration. The advantages for embryo sexing of testing for a DNA sequence that is repeated on the Y chromosome have been detailed previously (18,19).

A report of a repeated DNA sequence that is found on the Y chromosome of horses (20) concerns a short DNA sequence element known as Bkm (5'-G.A.C/T.A-3'; 21–23) that has been reported in many vertebrate species. It is also abundant elsewhere in the genome, to the extent that representatives on the Y chromosome comprise a small minority of the total. Such a sequence, of itself, has no utility in the diagnosis of genetic sex in microscopic biopsies.

SUMMARY OF THE INVENTION

The present inventors have now identified specific DNA sequences that are repeated in the Y chromosome of the horse. The nucleic acid isolates correspond to all or part of a DNA sequence found on the Y chromosome of *Equus caballus*. The present invention therefore provides a number of polynucleotide isolates capable of specifically hybridizing to samples of nucleic acid derived from horses which contain Y chromosomal DNA sequences.

A procedure similar in essence to that used in the first part of the present invention has been applied previously to animals where it was used to observe, but not isolate or otherwise define, DNA fragments associated with the heterogametic sex of chicken (24), cattle (25) and sheep (26).

Accordingly, in a first aspect the present invention provides an isolated polynucleotide, the polynucleotide having a sequence as set out in any one of SEQ ID NOS: 1 to 4 or 8 to 11, or a sequence which hybridizes thereto.

The polynucleotide sequences of the present invention hybridize specifically to the equine Y chromosome. By "hybridize specifically to the equine Y chromosome" we mean the polynucleotides hybridize to a repeat sequence which is present on the equine Y chromosome in a substantially greater copy number than is present elsewhere in the equine genome. Preferably, the sequence is present in less than six copies and more preferably in only one copy in the haploid female genome.

In a preferred embodiment the polynucleotide sequence has a sequence as set out in SEQ ID NO: 3 or a sequence which hybridizes thereto.

The polynucleotide sequences of the present invention preferably hybridize to sequences set out in SEQ ID NOS: 1 to 4 or 8 to 11 under high stringency. When used herein, "high stringency" refers to conditions that (i) employ low ionic strength and high temperature for washing after hybridization, for example, 0.1×SSC and 0.1% (w/v) SDS at 50° C.; (ii) employ during hybridization conditions such that the hybridization temperature is 25° C. lower than the duplex melting temperature of the hybridizing polynucleotides, for example 1.5×SSPE, 10% (w/v) polyethylene glycol 6000 (27), 7% (w/v) SDS (28), 0.25 mg/ml fragmented herring sperm DNA at 65° C.; or (iii) for example, 0.5M sodium phosphate, pH 7.2. 5 mM EDTA. 7% (w/v) SDS (28) and 0.5% (w/v) BLOTTO (29.30) at 70° C.: or (iv) employ during hybridization a denaturing agent such as formamide (31), for example, 50% (v/v) formamide with 5×SSC, 50 mM sodium phosphate (pH 6.5) and 5×Denhardt's solution (32) at 42° C.; or (v) employ, for example, 50% (v/v) formamide, 5×SSC, 50 mM sodium phosphate (pH 6.8), 0.1% (w/v) sodium pyrophosphate, 5×Denhardt's solution (32). Sonicated salmon sperm DNA (50 µg/ml) and 10% dextran sulphate (33) at 42° C. See generally references 34–36.

In a further preferred embodiment, the polynucleotide which hybridises under stringent conditions is less than 500 nucleotides, more preferably less than 200 nucleotides, and more preferably less than 100 nucleotides in length.

In a further preferred embodiment, the polynucleotide sequences of the present invention share at least 40% homology, more preferably at least 60% homology, more preferably at least 80% homology, more preferably at least 90% homology and more preferably at least 95% homology with a sequence shown in any one of SEQ ID NOS: 1 to 4 or 8 to 11, wherein the homology is calculated by the BLAST program blastn as described in Altschul, S. F., Madden, T. L., Schaffer, A. A., Zhang, J., Zhang, Z., Miller, W. And Lipman, D. J. (1997) "Gapped BLAST and PSI-BLAST: a new generation of protein database search programs", Nucleic Acids Research 25(17):3389–3402.

In a further preferred embodiment, the polynucleotide sequence of the present invention hybridises under stringent conditions to a sequence characterised by nucleotides 990–2497 of SEQ ID NO: 8, 421–1920 of SEQ ID NO. 9, 421–1930 of SEQ ID NO. 10, or 1502–2996 of SEQ ID NO. 11.

The polynucleotide of the present invention may comprise DNA or RNA sequences.

The present invention also provides a vector including a polynucleotide sequence according to the first aspect of the present invention and a host cell transformed with such a vector.

In a second aspect, the present invention provides an oligonucleotide probe or primer of at least 8 nucleotides, the oligonucleotide having a sequence that hybridizes to a polynucleotide of the first aspect of the present invention.

In a preferred embodiment the oligonucleotide is at least 10, more preferably at least 15 and more preferably at least 18 nucleotides in length.

In one preferred embodiment the oligonucleotide is derived from the sequence shown in SEQ ID NO:3. In one preferred embodiment the oligonucleotide comprises the sequence:

5'-AGCGGAGAAAGGAATCTCTGG-3' (SEQ ID NO: 12) or

5'-TACCTAGCGCTTCGTCCTCTAT-3' (SEQ ID NO: 13) derived from nts 6–26 and the reverse complement of nts 184–205, respectively, of the equine male genomic DNA sequence shown in SEQ ID NO: 7.

It will be appreciated that the probes or primers of the present invention may be produced by in vitro or in vivo synthesis. Methods of in vitro probe synthesis include organic chemical synthesis processes or enzymatically mediated synthesis, e.g. by means of SP6 RNA polymerase and a plasmid containing a polynucleotide sequence according to the first aspect of the present invention under transcriptional control of an SP6 specific promoter.

In a further preferred embodiment the oligonucleotide probe is conjugated with a label such as a radioisotope, an enzyme, biotin, a fluorescer or a chemiluminescer.

In a third aspect, the present invention provides a method of determining the sex of a horse, an equine fetus, an equine embryo or an equine cell(s) which method includes analysing a biological sample derived from the horse or the fetus or embryo or the population of cells, for the presence of a polynucleotide according to the first aspect of the present invention.

The equine cell(s) may be, for example, the sperm cells of a horse. In a preferred embodiment they may be populations of sperm cells or individual sperm cells that have been resolved by flow cytometry after staining with the fluorescent DNA-binding dye Hoechst 33342 (37,38).

The equine cell(s) may further be, for example, nucleated fetal cells. Such cells may be collected by amniocentesis or chorionic villus sampling. In a preferred embodiment they may be sampled in the peripheral blood of a pregnant mare (see generally reference 39 the disclosure of which is incorporated herein by reference).

In order to minimise the possibility of false negatives, the method is preferably conducted with one or more suitable positive controls. For example, the biological sample may be simultaneously analysed for the presence of a sequence which is present in approximately equal copy numbers in male and female horses. The biological sample may be analysed, for example, for the presence of a dispersed autosomal repeated sequence.

It will be understood by a person skilled in this field that an analysis to determine whether a sample contains the polynucleotide sequence of the present invention may be performed in a number of ways. For example, the analysis may involve Southern blot hybridization, dot blot hybridization or in situ hybridization tests using probes according to the present invention. Alternatively, the analysis may involve the technique of polymerase chain reaction (PCR; 16) or ligation amplification reaction (LAR: 40,41) using oligonucleotide primers and probes of the present invention.

The term "polymerase chain reaction" or "PCR" when used herein generally refers to a procedure where minute amounts of a specific piece of nucleic acid, RNA and/or DNA, are amplified as described in references 42 and 43. Generally, sequence information from the ends of the region of interest or beyond needs to be available, such that oligonucleotide primers can be designed; these primers will be identical in sequence or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally references 16 and 44.

As used herein, PCR is considered to be one, but not the only, example of a nucleic acid polymerase reaction method for amplifying a nucleic acid test sample, comprising the use of an established nucleic acid (DNA or RNA) as a primer, and utilises a nucleic acid polymerase to amplify or generate a specific piece of nucleic acid or to amplify or generate a specific piece of nucleic acid which is complementary to a particular nucleic acid (see, for example, references 45 and 46).

The terms "ligation chain reaction" or "LCR" or "ligation amplification reaction" or "LAR" when used herein generally refer to a procedure where minute amounts of a specific piece of nucleic acid, RNA and/or DNA, are amplified as described in references 40 and 41. Generally, sequence information from the region of interest needs to be available, such that oligonucleotide pairs can be designed that are complementary to adjacent sites on an appropriate nucleic acid template. The oligonucleotide pair is ligated together by the action of a ligase enzyme. The amount of ligated product may be increased by either linear or exponential amplification using sequential rounds of such template-dependent ligation. In the case of linear amplification, a single pair of oligonucleotides is ligated, the reaction is heated to dissociate the ligation product from its template, and similar additional rounds of ligation are performed. Exponential amplification utilises two pairs of oligonucleotides, one pair being complementary to one strand of a target sequence and the other pair being complementary to the second strand of the target sequence. In this case the products of ligation serve as mutually complementary templates for subsequent rounds of ligation, interspersed with heating to separate the ligated products from the template strands. A single basepair mismatch between the annealed oligonucleotides and the template prevents ligation, thus allowing the distinction of single base-pair differences between DNA templates. LAR can be used to amplify specific RNA sequences, specific DNA sequences from total genomic DNA, and cDNA transcribed from total cellular RNA, bacteriophage or plasmid sequences, etc. See generally references 40 and 41. As used herein, LAR is considered to be one, but not the only, example of a nucleic acid ligase reaction method for amplifying a nucleic acid test sample, comprising the use of an established nucleic acid (DNA or RNA) as a primer/probe, and utilises a nucleic acid ligase to amplify or generate a specific piece of nucleic acid or to amplify or generate a specific piece of nucleic acid which is complementary to a particular nucleic acid (see, for example, references 47 and 48).

In a fourth aspect, the present invention provides a kit for sex determination of a horse, an equine fetus, an equine embryo, an equine cell or a population of equine cells, which kit includes a polynucleotide according to the first aspect of the present invention or an oligonucleotide probe or primer according to the second aspect of the present invention.

The terms "EY.AC6", "EY.AD11", "EY.AI5" and "EY.AM7" as used herein refer to, where provided, the specific DNA sequences set forth in SEQ ID NOS: 1–4 respectively. These terms also include variants where nucleotides have been substituted, added to or deleted from the relevant sequences shown in SEQ ID NOS: 1–4 so long as the variants hybridize specifically to the equine Y chromosome.

Such variants may be naturally occurring variants which may arise within an individual or a population by virtue of point mutation(s), deletion(s) or insertion(s) of DNA sequences, by recombination, gene conversion, flawed replication or rearrangement. Alternatively, such variants may be produced artificially, for example by site-directed mutagenesis, by "gene shuffling", by deletion using exonuclease(s) and/or endonuclease(s), or by the addition of DNA sequences by ligating portions of DNA together, or by the addition of DNA sequences by template-dependent and/or template-independent DNA polymerase(s).

The EY.AC6 DNA sequence is shown in SEQ ID NO: 1. The sequence, comprising 432 base pairs of nucleotides, was determined from a fragment of DNA that was cloned into plasmid pGEM-T (trademark Promega). The cloned fragment had been recovered from a polyacrylamide gel following electrophoresis and staining of the products of RAPD PCR of male equine genomic DNA with Operon (trademark) primer OPAC.06. The fragment was selected because it was visible as a product of RAPD PCR of male but not female genomic DNA. Homologues of the cloned fragment EY.AC6 have been shown, by its hybridization to Southern blots of genomic DNA from male and female *Equus caballus*, to be present in both sexes but are repeated at much higher amounts in males, with the haploid female genome containing just one or a small number of copies. The defined sequence EY.AC6 appears to be contiguous with sequence EY.AM7 in the equine Y chromosome since the two sequenced isolates share a region of overlap of 128 bp with 91% similarity.

The EY.AD11 DNA sequence is shown in SEQ ID NO: 2. The sequence, comprising 600 base pairs of nucleotides, was determined from a fragment of DNA that was cloned into plasmid pGEM-T (trademark Promega). The cloned fragment had been recovered from a polyacriylamide gel following electrophoresis and staining of the products of RAPD PCR of male equine genomic DNA with Operon (trademark) primer OPAD.11. The fragment was selected because it was visible as a product of RAPD PCR of male but not female genomic DNA. Homologues of the cloned fragment EY.AD11 have been shown, by its hybridization to Southern blots of genonlic DNA from male and female *Equus caballus*, to be present in both sexes but are repeated at much higher amounts in males, with the haploid female genome containing just one or a small number of copies.

The EY.AI5 DNA sequence is shown in SEQ ID NO: 3. The sequence, comprising 230 base pairs of nucleotides, was determined from a fragment of DNA that was cloned into plasmid pGEM-3Z (trademark Promega). The cloned fragment had been recovered from a polyacrylamide gel following electrophoresis and staining of the products of RAPD PCR of male equine genomic DNA with Operon (trademark) primer OPAI.05. The fragment was selected because it was visible as a product of RAPD PCR of male but not female genomic DNA. Homologues of the cloned fragment EY.AI5 have been shown, by its hybridization to Southern blots of genomic DNA from male and female *Equus caballus*, to be present in both sexes but are repeated at much higher amounts in males, with the haploid female genome containing just one or a small number of copies.

The EY.AM7 DNA sequence is shown in SEQ ID NO: 4. The sequence, comprising 285 base pairs of nucleotides, was determined from a fragment of DNA that was cloned into plasmid pGEM-T (trademark Promega). The cloned fragment had been recovered from a polyacrylamide gel following electrophoresis and staining of the products of RAPD PCR of male equine genomic DNA with Operon (trademark) primer OPAM.07. The fragment was selected because it was visible as a product of RAPD PCR of male but not female genomic DNA. Homologues of the cloned fragment EY.AM7 have been shown, by its hybridization to Southern blots of genomic DNA from male and female *Equus caballus*, to be present in both sexes but are repeated at much higher amounts in males, with the haploid female genome containing just one or a small number of copies. The defined sequence EY.AM7 appears to be contiguous with sequence EY.AC6 in the equine Y chromosome since the sequences isolated share a region of overlap of 128 bp with 91% similarity.

The DNA sequences described herein (SEQ ID NOS: 1–4) were determined by chain-termination DNA sequencing techniques (49) using fluorescence-labelled dideoxynucleotides (50–53).

It will be appreciated by those skilled in the art that the polynucleotide sequences of the present invention are advantageous in that they are present in multiple copies on the Y chromosome, thereby providing greater sensitivity in assays for the presence of a Y chromosome than is possible when the assay involves detection of a unique (single copy) DNA sequence. This allows detection to be applied with greater facility to very small samples, as in a few cells removed from a viable embryo (2) or cells of fetal origin in peripheral blood of a pregnant mare (39) or sperm cells separated by fluorescence activated cell sorting (38).

The polynucleotide sequences and oligonucleotide primers and probes of the present invention have application, for example, in sexing of embryo biopsy; fetal sex detection, i.e. by amniocentesis, chorionic villus sampling, fetal cells circulating in peripheral blood of a pregnant mare; analysis of the sex chromosome constitution of an individual sperm cell or of populations of sperm cells; resolution of ambiguities in sexual phenotype; sex analysis of tissues derived from horses (meat, hide, hair, bone, etc. from living or dead horses); and similar applications in related equine species, including extinct or endangered species.

The polynucleotide sequences and oligonucleotide primers and probes of the present invention also have a variety of uses in addition to their use in sexual identification. For example, the sequences may be used to screen recombinant DNA libraries prepared from a variety of mammalian species. The DNA sequences may be used to deduce similar sequences or genetically linked sequences having similar functionality. The sequences may also be used in chromosome walking or jumping techniques to isolate coding and non-coding sequences proximal to the nucleotide sequence of the present invention.

According to a further aspect of the present invention, there is provided a method for the isolation of Y-chromosomal DNA sequences comprising:

pooling equivalent amounts of genomic DNA from a number of male animals of a single species and pooling equivalent amounts of genomic DNA from a similar number of female animals of the same species, with the female animals preferably being related closely to the male animals, e.g. siblings;

subjecting equivalent samples of the male and female pooled DNA mixtures to PCR with an arbitrary oligonucleotide primer and resolving the resultant fragments by gel electrophoresis;

examining the stained resolved products for fragments that are amplified from male DNA but not from female DNA;

recovering said fragment(s) from an electrophoresis gel and isolating individual fragments by molecular cloning; and PCR analysis of samples of male and female genomic DNA using oligonucleotide primers derived from the DNA sequence of said isolated fragment(s).

In a preferred embodiment the method includes the additional step after step (iii) of confirming the male association of fragment(s) by PCR and electrophoretic analysis of equivalent genomic DNA samples from a number of individual male and female animals. Preferably the method also includes an additional step after step (iv) of confirming the isolation of individual male-associated fragment(s) by hybridization of the labelled said fragment(s) with samples of male and female genomic DNA.

The terms "comprise", "comprises" and "comprising" as used throughout the specification are intended to refer to the inclusion of a stated component or feature or group of components or features with or without the inclusion of a further component or feature or group of components or features.

The present invention will now be described, by way of example only, with reference to the following non-limiting drawings and examples.

BRIEF DESCRIPTION OF THE FIGURES

FIG. 2 shows the sequence of fragments amplified directly from genomic DNA of male and female horses using primers EQYL1 and EQYR1. Differences between the sequences determined from male and female genomic DNA are indicated by *; differences between the cloned EY.AI5 sequence (SEQ ID NO: 3) and the sequence from male genomic DNA are indicated by *. The underlined region from nt 6 to nt 26 is the sequence of sexing primer EQYL2; the underlined region from nt 184 to nt 205 is the reverse complement of the sequence of sexing printer EQYR5 (refer to text).

FIG. 3 shows hybridization analysis of recombinant phage DNA with cloned male-associated sequences. Samples of DNA (10 μg) of Lambda Fix® II vectors containing equine genomic inserts were digested with restriction enzymes EcoRI and HindIII as shown. Digests were treated at 68° C. for 15 min then resolved by agarose gel electrophoresis before transfer to positively-charged nylon membrane as described in the text. The membrane was hybridized with digoxigenin-labelled probes prepared by PCR amplification of cloned inserts from the flanking plasmid primers SP6 and T7. One probe was stripped from the membrane by methods described in the text before hybridization with the second probe. The inserts used as probes were: (a) EY.AI5; (b) EY.AD11. A photograph of the gel taken under uv transillumination before DNA transfer is shown. The lanes labelled M contained DNA standards whose sizes are indicated in base pairs.

BRIEF DESCRIPTION OF SEQUENCE LISTINGS

SEQ ID NO: 1 shows the sequence of one strand of equine repeat element EY.AC6 comprising 432 complementary base pairs. The sequence is written in single-letter code from the 5'-terminus to the 3'-terminus according to standard practice.

SEQ ID NO: 2 shows the sequence of one strand of equine repeat element EY.AD11 comprising 600 complementary base pairs.

SEQ ID NO: 3 shows the sequence of one strand of equine repeat element EY.AI5 comprising 230 complementary base pairs.

SEQ ID NO: 4 shows the sequence of one strand of equine repeat element EY.AM7 comprising 285 complementary base pairs.

SEQ ID NO: 5 shows the sequence of the cloned EY.AI5 sequence

SEQ ID NO: 6 shows the sequence of fragments amplified directly from genomic DNA of female horses using primers EQYL1 and EQYR1.

SEQ ID NO: 7 shows the sequence of fragments amplified directly from genomic DNA of male horses using primers EQYL1 and EQYR1.

Figure 4A:
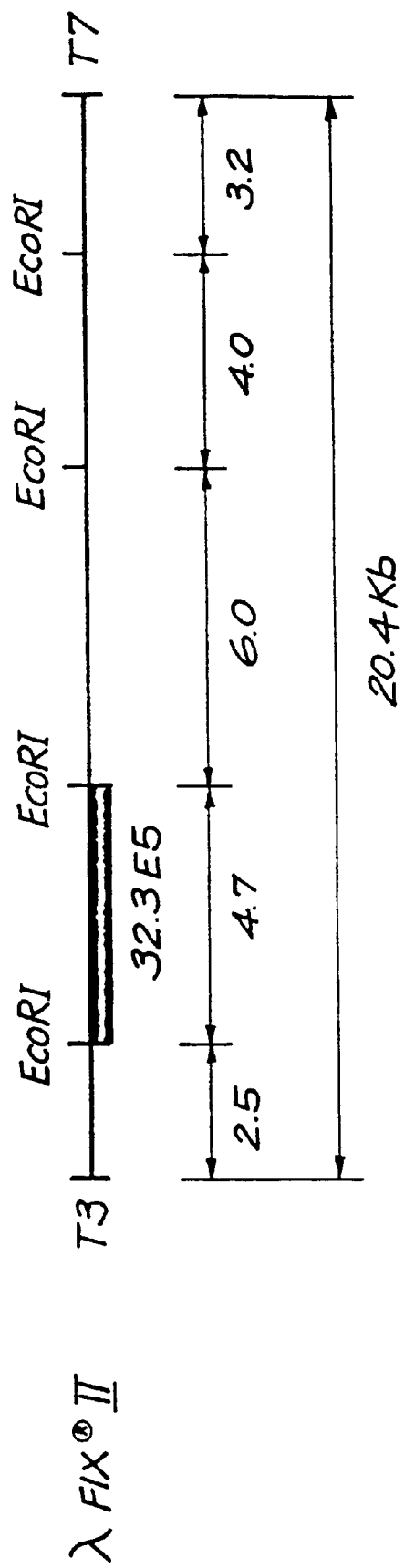
FIG. 4 shows in (a) the sites for restriction enzyme EcoRI in the equine genomic DNA insert 32.3 after excision of the insert, together with its flanking T3 and T7 promoter sequences, from the Lambda Fix® II vector with the restriction enzyme NotI. The position of 4.7 kb subcloned EcoRI fragment 32.3E5 is indicated. The complete sequence of 32.3E5 was determined and, in (b), the positions of previously described sequences EY.AC6, EY.AD11, EY.AI5 and EY.AM7 within the subclone are illustrated, as is the relative position of the truncated LINE repeat EY.LINE as defined in the text. There is a close relationship between the DNA sequences of subclone 32.3E5 and subclone 33.1H7 (see FIG. 5) which allows 33.1H7 to be superimposed on 32.3E5 as shown.

SEQ ID NO: 8 shows the sequence of one strand of subclone 32.3E5 comprising 4693 complementary base pairs of equine genomic DNA. Subclone 32.3E5 is an EcoRI fragment of recombinant phage 32.3. The position of the fragment within the phage insert is shown in FIG. 4a.

Figure 5A:
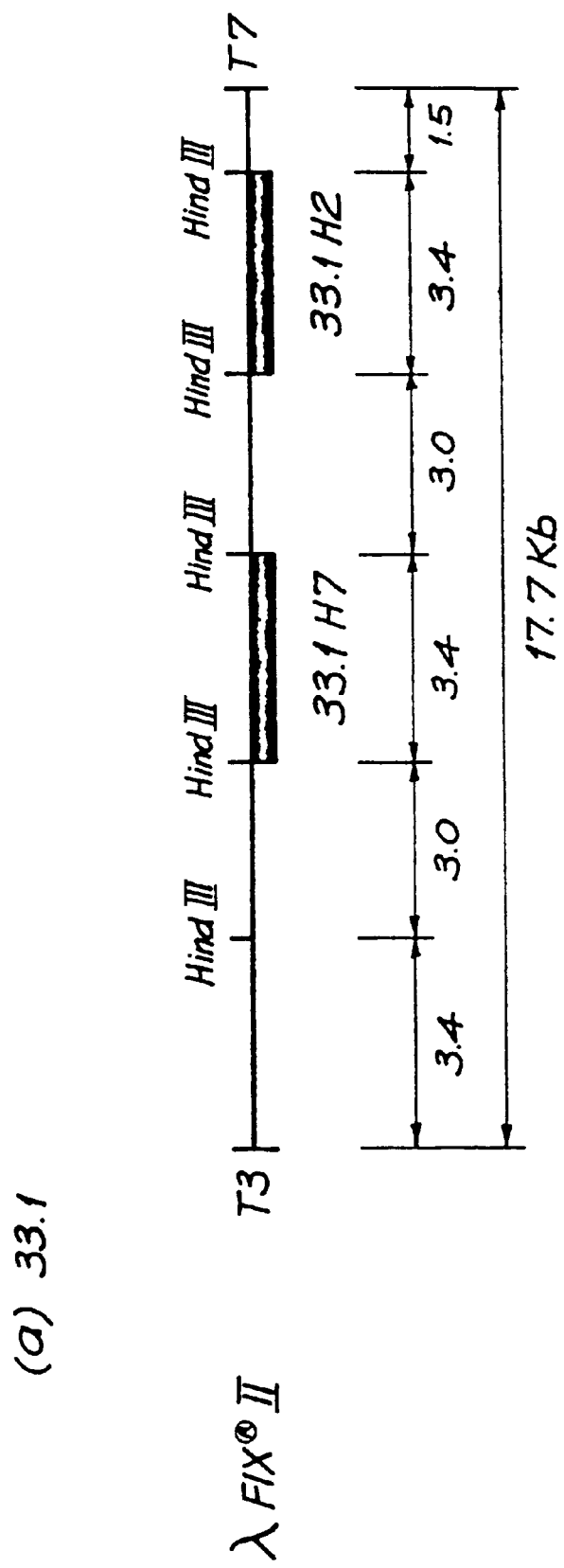
FIG. 5 shows in (a) the sites of restriction enzyme HindIII in the genomic DNA insert 33.1 after excision of the insert, together with its flanking T3 and T7 promoter sequences, from the Lambda Fix® II vector with the restriction enzyme NotI. The locations of two 3.4 kb subcloned repeated HindIII fragments 33.1H7 and 33.1H2 are indicated although it was not possible to determine which repeat occupied either of the two possible positions. The complete sequences of both fragments were determined and found to have 88–90% identity. In (b), the positions of previously described sequences EY.AC6, EY.AD11, EY.AI5 and EY.AM7 within the subclone 33.1H7 are illustrated, as is the relative position of the truncated LINE repeat EY.LINE as defined in the text. There is a close relationship between the DNA sequences of subclone 32.3E5 and subclone 33.1H7 which allows 33.1H7 (and 33.1H2) to be superimposed on 32.3E5 as shown in FIG. 4b.

SEQ ID NO: 9 shows the sequence of one strand of subclone 33.1H7 comprising 3430 complementary base pairs of equine genomic DNA. Subclone 33.1H7 is one of two repeated HindIII fragments of recombinant phage 33.1 and is 88–90% homologous with a second HindIII fragment, 33.1H2 (detailed in SEQ ID NO:10). The position of the repeated fragment within the phage insert is shown in FIG. 5a.

SEQ ID NO: 10 shows the incomplete sequence of one strand of subclone 33.1H2 comprising 3230 complementary base pairs of equine genomic DNA, from 1 to 2122 and from 2342 to 3450 of the subclone. Subclone 33.1H2 is the second of two repeated HindIII fragments of phage 33.1 and is 88–90% homologous with the HindIII fragment, 33.1H7 (detailed in SEQ ID NO: 9). The position of the repeated fragment within the phage insert is shown in FIG. 5a.

Figure 6A:
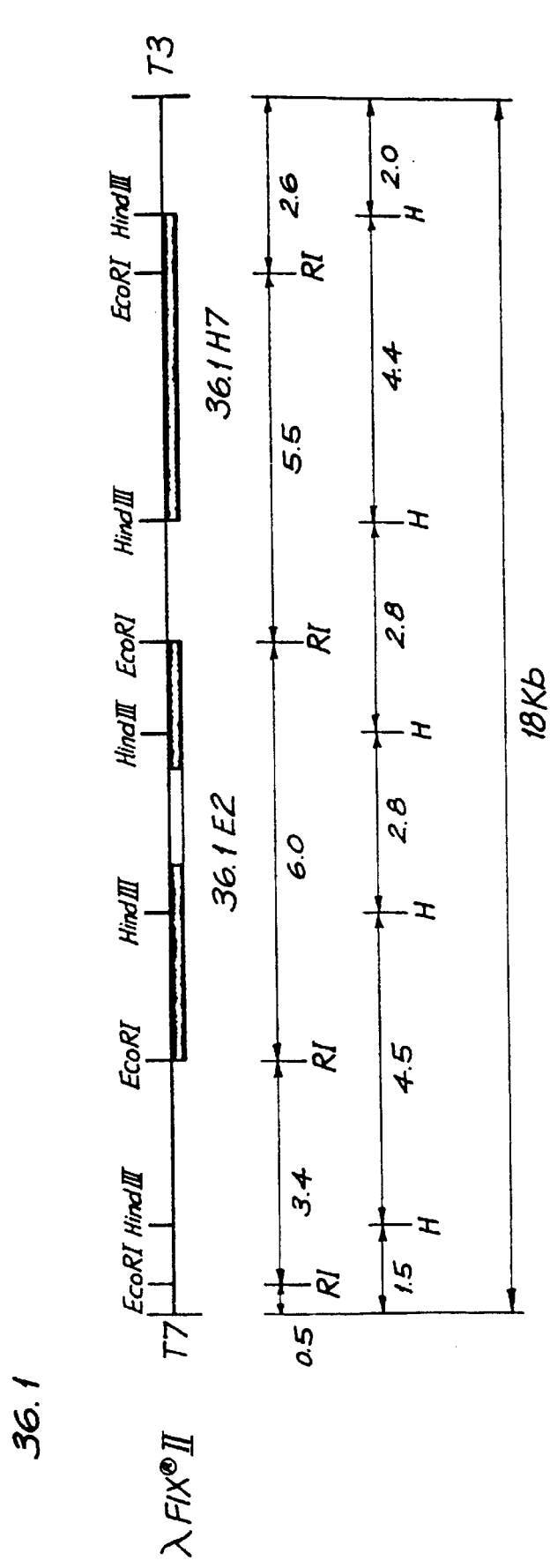
FIG. 6 shows in (a) the sites of restriction enzymes EcoRI and HindIII in the equine genomic DNA insert 36.1 after excision of the insert, together with its flanking T3 and T7 promoter sequences, from the Lambda Fix® II vector with the restriction enzyme NotI. The position of 6.0 kb subcloned EcoRI fragment 36.1E2 is indicated, as is the position of 4.4 kb subcloned HindIII fragment 36.1H7. The complete sequence of 36.1H7 was determined and, in (b), the positions of previously described sequences EY.AC6, EY.AD11, EY.AI5 and EY.AM7 within the subclone are illustrated, as is the relative position of the truncated LINE repeat EY.LINE as defined in the text. There is a close relationship between DNA sequences from base 1378 to base 4355 of subclone 36.1H7 to sequences in subclone 32.3E5 (see FIG. 4b) and subclones 33.1H7 and 33.1H2 (see FIG. 5b). Sequence in subclone 36.1H7 located 5' to this homologous region encoded inverted and direct repeats of EY.AC6, EY.AD11 and intervening sequence.

SEQ ID NO: 11 shows the sequence of one strand of subclone 36.1H7 comprising 4355 complementary base pairs of equine genomic DNA. Subclone 36.1H7 is a HindIII fragment of phage 36.1. The position of the fragment within the phage insert is shown in FIG. 6a.

SEQ ID NO: 12 shows an oligonucleotide probe (EQYL2) derived from SEQ ID NO:3.

SEQ ID NO: 13 shows an oligonucleotide probe (EQYR5) derived from SEQ ID NO:3.

SEQ ID NO: 14 shows an oligonucleotide primer (EQYR4) derived from SEQ ID NO:3.

SEQ ID NO: 15 shows an oligonucleotide primer (EQYL1) derived from SEQ ID NO:3.

SEQ ID NO: 16 shows an oligonucleotide primer (EQYR1) derived from SEQ ID NO:3.

SEQ ID NO: 17 shows an oligonucleotide primer (EQSIN8) derived from SEQ ID NO:3.

SEQ ID NO: 18 shows all oligonucleotide primer (EQSIN9) derived from SEQ ID NO:3.

SEQ ID NO: 19 shows an oligonucleotide primer (mEQYL2) derived from SEQ ID NO:3.

SEQ ID NO: 20 shows an oligonucleotide primer (mEQYR5) derived from SEQ ID NO: 3.

SEQ ID NO: 21 shows an oligonucleotide primer (mEQSIN8) derived from SEQ ID NO:3.

SEQ ID NO: 22 shows an oligonucleotide primer (mEQSIN9) derived from SEQ ID NO:3.

Definitions and Abbreviations
ATP adenosine-5'-triphosphate
BLOTTO skim milk powder
bp base pairs
ccc covalently closed circular
cfu colony-forming units
BSA bovine serum albumin
Denhardt's solution 0.02% (w/v) BSA, 0.02% (w/v) Ficoll 400, 0.02% (w/v) PVP
DIG digoxigenin
DNA deoxyribonucleic acid
dNTP deoxynucleotide triphosphate (dATP, dCTP, dGTP, dTTP)
DTT dithiothreitol
EDTA ethylenediaminetetraacetic acid
g force of gravity
h hour(s)
LAR ligation amplification reaction
LB Luria-Bertani
mg milligram(s)=$10^{-3}$ gram
min minute(s)
ml milliliter(s)=$10^{-3}$ liter
μg microgram(s)=$10^{-6}$ gram
μl microliter(s)=$10^{-6}$ liter
ng nanogram(s)=$10^{-9}$ gram
nm nanometer=$10^{-9}$ meter (ref. wavelength of light)
nt(s) nucleotide(s)
oligonucleotide single-stranded DNA<30 nts
PAGE polyacrylamide gel electrophoresis
PBS phosphate-buffered saline=100 mM NaCl, 2.7 mM KCl, 1.75 mM $KH_2PO_4$, 4.3 mM $Na_2HPO_4$, pH 7.4

PCR polymerase chain reaction
pg picogram(s)=$10^{-12}$ gram
polynucleotide single- or double-stranded DNA or RNA
primer oligonucleotide used to prime PCR
probe (labelled) nucleic acid that hybridizes to specific target sequence(s)
PVP polyvinylpyrrolidone
RAPD random amplification of polymorphic DNA
RNA ribonucleic acid
rpm revolutions per minute
SDS sodium dodecylsulphate
SINE short interspersed repetitive element
SSC standard saline-citrate=0.15 M NaCl, 15 mM trisodium citrate
SSPE standard saline-phosphate-EDTA=0.18M NaCl, 10 mM $NaH_2PO_4$, 1 mM EDTA, pH 7.7
TAE tris-acetate-EDTA=40 mM tris-acetate, 2 mM acetic acid, 10 mM EDTA, pH 8.4
Taq *Thermus aquaticus*
TBE tris-borate-EDTA=89 mM tris-HCl, 0.89M sodium borate, 2 mM EDTA, pH 8.4
TE tris-EDTA=10 mM tris-HCl, 1 mM EDTA, pH 7.5
TEMED N,N,N',N'-tetramethylethylenediamine
temp temperature
tris tris(hydroxymethyl)-aminomethane
uV ultraviolet
V volts
vol volume equivalent
v/v volume/volume equivalent

DETAILED DESCRIPTION OF THE INVENTION

Example 1

Preparation Of Genomic DNA From Equine Blood Samples: Equine blood samples were collected into 10 ml EDTA Vacutainers®, placed immediately on ice and delivered to the laboratory within two days. It was found that samples could be stored in a Vacutainer® at 4° C. for up to six months without significant loss of yield or quality of DNA extracted therefrom.

Twenty five ml of cold lysis buffer (0.32M sucrose, 10 mM tris-HCl, pH 7.5, 5 mM $MgCl_2$, 1% (v/v) Triton X-100) was added to 10 ml of whole blood. The suspension was centrifuged at 4000×g for 20 min at 4° C. and the pelleted cells were resuspended in PBS and recentrifuged. The cells were then suspended in 9 ml of TE. The suspension was adjusted to 25 mM EDTA, 0.5% (w/v) SDS and 0.1 mg/ml of proteinase K (Boehringer Mannheim) and the lysed mixture was incubated overnight at 37° C. with gentle agitation. The digested sample was extracted with 5 ml of phenol/chloroform (equal volumes of phenol equilibrated with tris-HCl/EDTA (Sigma) and 24:1 (v/v) chloroform/isoamyl alcohol) for 60 min and the mixture was centrifuged at 4000×g for 25 min at 25° C. The aqueous phase was removed from each tube and transferred to a clean tube.

DNA was precipitated by the addition of 2.5 vol ethanol or 1 vol propanol, the supernatant decanted and the DNA pellet rinsed with 0.5 ml of 70% (v/v) ethanol and air-dried. The DNA was finally dissolved in 2 ml of 0.1×TE and stored at −20° C.

DNA concentrations were determined using a Pharmacia Gene Quant RNA/DNA calculator. The yield was typically 50–250 µg of high molecular weight DNA (estimated by ethidium staining after agarose gel electrophoresis).

Conceptual Basis for Identification of Male-Associated DNA

The Y chromosome is the sole genetic difference between male and female horses, being present in all nucleated cells of normal males and absent from the cells of normal females. This genetic difference must be reflected in the presence of Y-chromosomal DNA sequences in the male genome that are absent from the female genome. It would be expected that Y-chromosomal, male-specific DNA sequences could be identified by a technique that surveys multiple genomic DNA sequences at random (54), by comparing survey data from normal male and female genomes which are in all other respects identical.

It was not possible to obtain isogenic male and female horses, i.e. individuals whose genomes are identical except for the Y chromosome of the male (cf. inbred strains of mice). In the absence of genetic homology, a combination of statistical and genetic techniques was used to generate pseudo-isogenic samples of male and female equine DNA.

DNA was extracted from white blood cells of nine brother-sister sibling pairs and equal amounts of DNA from each of the nine males were pooled to provide a sample of male DNA. Equal amounts of DNA from each of their sisters were pooled to provide a parallel sample of pseudo-isogenic female DNA.

RAPD PCR Of Pooled DNA Samples

The pooled mixtures of male and female DNA were surveyed for male-associated sequence differences by PCR amplification, using decanucleotide primers known as RAPD primers that are available commercially from Operon Technologies.

The method used for RAPD PCR was adapted from a method described previously (55). Each PCR reaction contained 25 ng of equine genomic DNA, 5 µM RAPD primer (Operon Technologies), 3 units of Taq DNA polymerase Stoffel fragment (Perkin-Elmer), 200 µM of each of the four dNTPs (Promega), 10 mM tris-HCl, pH 8.0, 10 mM KCl and 5 mM $MgCl_2$ in a total volume of 20 µl.

Reactions were cycled in a Corbett Research PC-960 Air-Cooled Thermocycler with an initial step of 94° C. for 5 min followed by 35 cycles consisting of 94° C. for 30 sec then 1 min at each of 57° C., 56° C., 55° C., 54° C. and 53° C.; on completion of cycling the samples were heated at 72° C. for 5 min.

Electrophoretic Analysis of RAPD PCR Products

Polyacrylamide gel electrophoresis was used to resolve the products of RAPD PCR, greatly increasing the resolution of fragments relative to that attainable by agarose gel electrophoresis. Silver staining enhanced the sensitivity of detection compared with uv fluorescence of ethidium bromide.

DNA amplification products were resolved by polyacrylamide gel electrophoresis (PAGE) in a Bio-Rad Mini-Protean II. The polyacrylamide gels were 10% (w/v) acrylamide and 2% (w/v) bis-acrylamide in TBE buffer containing 10% (w/v) urea and 5% (v/v) glycerol. Ammonium persulphate (0.15% w/v) and TEMED (0.15% v/v) were used to initiate and catalyse polymerisation.

The 0.5 mm gels were cast on Gel Bond PAG backing film (FMC; 56). Samples (2 µl) of PCR reaction product were mixed with 1 µl of loading buffer (40% (w/v) urea, 3% (w/v) Ficoll 400, 10 mM tris-HCl, pH 8.0, 3 mM EDTA, 0.02% (w/v) xylene cyanol, 0.02% (w/v) bromophenol blue), loaded into pre-formed slots and electrophoresed in TBE buffer at 300V for 40 min. Resolved DNA fragments were visualised by silver staining (57).

In total, 216 different Operon RAPD primers were used to screen the pooled pseudo-isogenous samples of male and female DNA. of which 90% yielded clear, reproducible results for both pooled samples.

Identification of Male-Associated DNA Fragments

Nineteen of the 216 tested primers were found to amplify a fragment from the male DNA pool that was either less intense than a fragment of similar size in the female DNA pool or apparently absent from the PCR products of the female DNA pool. To determine whether candidate fragments were indeed amplified from the DNA of all males and only males, primers yielding candidate male-associated fragments from the pooled DNA samples were used for RAPD PCR of DNA isolated from a number of individual males and females. A fragment amplified differentially from pooled male DNA could arise from an autosomal polymorphism in one or two individuals, a possibility confirmed by the occasional observation of differential RAPD PCR fragments from the pooled female DNA sample.

The 19 candidate primers were used to amplify individual DNA samples from four male and four female horses. Unambiguous male-associated fragments were evident in the products from five of these primers: OPAC.06 (5'-CCAGAACGGA-3' (SEQ ID NO:23)), OPAD.11 (5'-CAATCGGGTC-3' (SEQ ID NO:24)), OPAI.05 (5'-GTCGTAGCGG-3' (SEQ ID NO:25)), OPAM.01 (5'-TCACGTACGG-3' (SEQ ID NO:26)) and OPAM.07 (5'-AACCGCGGCA-3' (SEQ ID NO:27)). The sizes of the differential fragments were estimated at approximately 460 bp, 530 bp, 240 bp, 320 bp and 300 bp, respectively.

Isolation of Male-Associated DNA Fragments

For each of the five candidate male-specific fragments, a slice containing the fragment was cut from the silver-stained polyacrylamide gel and allowed to stand in 20–50 µl of 0.1×TE at room temp for 60 min. Eluted DNA was re-amplified under the conditions described above for RAPD PCR using the relevant RAPD primer and 1 µl of excised fragment solution as template. Reactions were cycled in a Corbett Research PC-960 Air-Cooled Thermocycler with an initial step at 94° C. for 2 min followed by 35 cycles of 94° C. for 30 sec then 55° C. or 60° C. for 1 min; on completion of cycling the samples were heated at 72° C. for 2 min.

It was necessary to confirm that the re-amplified DNA samples corresponded in electrophoretic mobility with the candidate RAPD fragments and that each contained a male-associated DNA fragment. Accordingly, each re-amplified sample was electrophoresed on a polyacrylamide gel adjacent to the products of PRAP PCR of male and female genomic DNA with the relevant primer, and with the products of RAPD PCR from female DNA mixed with the re-amplified sample.

In each case, the re-amplified fragment migrated similarly to the fragment associated differentially with male DNA. In further confirmation, each of the re-amplified samples was labelled with digoxigenin and the resultant probes were hybridized to Southern blots of male and female horse genomic DNA that had been digested with the restriction enzyme Sau3AI. Each re-amplified fragment showed an unequivocal male-associated pattern of hybridization (data not shown; refer to "Colony Screening By Dot Blot Hybridization" for details of probe preparation, hybridization and detection). In each case the probe also hybridized with female genomic DNA, implying that the fragments may not be associated uniquely with the Y chromosome and/or the sample included contaminating non-Y-chromosomal DNA.

Re-amplified PCR products were electrophoresed in 1% (w/v) LMP agarose (Sigma) in 0.5×TBE buffer. The material recovered from PCR with the OPAI.05 primer was visualised by illumination at 302 nm of an ethidium bromide-stained gel. The material recovered from PCR of equine genomic DNA with the OPAC.06, OPAD.11, OPAM.01 and OPAM.07 primers were visualised by staining with crystal violet (58).

A minimal portion of gel containing the desired fragment was excised and melted at 70° C. in a 1.5 ml microcentrifuge tube. The molten gel slice was diluted with three volumes of TE and extracted with an equal volume of phenol (saturated with TE) at 70° C. for 2 mill. The tube was transferred to ice for 2 min then centrifuged at 14,000 rpm in an Eppendorf 5414C microcentrifuge for 4 min at room temp and the aqueous phase removed into a clean tube. The phenol phase was back-extracted with 50 µl of TE and this was combined with the original extracted aqueous phase.

DNA was precipitated by the addition of 0.1 vol of 3M sodium acetate. pH 5. and 2.5 vol ethanol. The tube was stored overnight at −20° C. then centrifuged at 13000 rpm in an Eppendorf 5414C microcentrifuge for 30 min at 4° C. The supernatant was decanted carefully, the DNA pellet was rinsed with cold 75% (v/v) ethanol and centrifuged briefly. The pellet was dried in a vacuum desiccator for 10 min and the DNA was finally dissolved in 20 µl of TE and stored at 4° C.

Ligation of PCR-Amplified Niale-Associated Fragments into Plasmid Vector

Fragments resulting from PCR with RAPD primers OPAC.06. OPAD.11. OPAM.01 and OPAM.07 were ligated into plasmid pGEM-T (a linearised derivative of pGEM-3) using the pGEM-T vector cloning system (Promega) according to the supplier's instructions.

Fragments resulting from PCR with RAPD primer OPAI.05 were cloned by blunt-end ligation into the plasmid vector pGem-3Z (Promega). The vector was linearised by digestion with restriction endonuclease SmaI (New England BioLabs) in NEBuffer 4 (New England BioLabs) then treated with calf alkaline phosphatase (New England BioLabs). The digested plasmid DNA was purified by electrophoresis in 1% (w/v) LMP agarose (Sigma) in 0.5×TBE buffer. The gel was stained with crystal violet (58), a minimal portion of gel containing the linear plasmid was excised and DNA was recovered as described above.

The gel-purified OPAI.05 male-associated RAPD material was treated with T4 DNA polymerase (New England BioLabs) according to the supplier's instructions then heated at 65° C. for 15 min. The cooled sample was then treated with T4 polynucleotide kinase (New England BioLabs) according to the supplier's instructions, then again heated at 65° C. for 15 min. The gel-purified linear vector (approx. 10 ng) and PCR fragments (approx. 5 ng) were ligated with 3 Weiss units of T4 DNA ligase (Promega) in 50 µl of Promega DNA ligase buffer (30 mM Tris-HCl, pH 7.8, 10 mM $MgCl_2$, 10 mM DTT, 0.5mM ATP) at 4° C. for 14–16 h.

Transformation with Recombinant Plasmids

Single colonies of *Escherichia coli* strain DH5a (fragments from RAPD PCR with primers OPAC.06, OPAD.11, OPAM.01 and OPAM.07) or strain XL1-Blue (fragments from RAPD PCR with primer OPAI.05) were inoculated into 200 ml of LB broth and grown in a shaking incubator at 37° C. to an optical absorbance of approx. 0.3 at 550 nm (3–4 h). The cells were collected by centrifugation at 3000 rpm for 5 min at 4° C. in an Eppendorf 5414C microcentrifuge, resuspended in 30 ml of cold 0.1M $MgCl_2$ and placed on ice for 20 min. The cells were collected by centrifugalion as before and the pellet suspended in 1 ml of cold 0.1M CaCl2. Glycerol was added to 15% (v/v) and the competent cells were stored at −70° C.

For transformation, 50 μl of competent cells was thawed and mixed with 5 μl of ligation reaction, placed on ice for 20 min. heat-shocked at 42° C. for 45 sec then returned to ice for 5 min. The transformed cells were allowed to recover by incubation at 37° C. for 1 h in 500 μl of SOC medium (2% (w/v) bacto-tryptone, 0.5% (w/v) bacto-yeast extract, 10 mM NaCl, 2.5 mM KCl, 10mM $MgCl_2$, 10 mM $MgSO_4$, 20 mM glucose) and were then plated onto LB agar containing ampicillin (100 μg/ml), X-gal (25 μg/ml) and IPTG (10 μM) for overnight culture at 37° C. Transformation efficiency was $2 \times 10^7$ cfu/μg plasmid (with ccc pGEM-T).

Colony Screening by PCR

White colonies were selected and incubated overnight in 500 μl of LB broth. Inserts in recombinant plasmids of the cloned cells were analysed by PCR amplification from primer sites flanking the cloning site. One 1 μl of the cell suspension was mixed with 2.7 μM each of the SP6 (5'-ATTTAGGTGACACTATAGAATAC-3' (SEQ ID NO:28)) and T7 (5'-ATTATGCTGAGTGATATCCCGCT-3' (SEQ ID NO:29)) primers (both from Bresatec Custom Oligos), 200 μM of each of the four dNTPs, 1.5 mM $MgCl_2$, 100 mM tris-HCl, pH 8.3, 500 mM KCl and 1 unit of Taq DNA polymerase (Boehringer Mannheim) in a final volume of 25 μl.

Reactions were cycled in a Corbett Research PC-960 Air-Cooled Thermocycler with an initial step at 94° C. for 2 min followed by 35 cycles of 94° C. for 20 sec, 50° C. for 20 sec and 72° C. for 30 sec; on completion of cycling the samples were heated at 72° C. for 2 min.

Colony Screening by Dot Blot Hybridization

Colonies that were found by PCR to contain a recombinant insert of appropriate size (i.e. appropriate to the size of the male-associated fragment generated from genomic DNA by RAPD PCR) were labelled by incorporating 8 μM digoxigenin-11-dUTP (DIG-dUTP: Boehringer Mannheim) in colony PCR reactions, as described above.

A replicate dilution series of male and female horse genomic DNA samples (1 μg, 250 ng, 100 ng and 10 ng of each) were denatured in 0.2 ml of 0.4M NaOH, 10 mM EDTA and heated at 100° C. for 10 min. The samples were applied to positively-charged nylon membrane (Boehringer Mannheim; 59) with a Vacuum Blot Manifold (Gibco-BRL). Each well was washed with 500 μl of 0.4M NaOH and the membrane was neutralised by 3×10 min washes in 2×SSC.

DNA hybridizations were performed according to the DIG System User's Guide for Filter Hybridization (Boehringer Mannheim). Membranes were prehybridized at 50° C. for at least 2 h in 10 ml of DIG Easy Hyb hybridization buffer (Boehringer Mannheim, cat. no. 1603558) in glass hybridization bottles (Hybaid) placed in a Eurotherm 91E Rotating Hybridization Incubator (Model 310; Robbins Scientific).

DIG-labelled probes were prepared as described above from the inserts of recombinant plasmids, using the SP6 and T7 primers. Each was added to 4 ml of DIG Easy Hyb solution (Boehringer Mannheim) at a concentration of 50–100 ng/ml and denatured at 68° C. for 10 min. The prehybridization solution was replaced by the probe solution and hybridization was conducted in the rotating incubator at 50° C. for 14–16 h.

The membrane was then removed and washed for 3×10 min at low stringency (2×SSC, 0.1% (w/v) SDS, 25° C.) followed by 2×10 min at high stringency (0.2×SSC, 0.1% (w/v) SDS, 68° C.). The washed membrane was rotary-incubated for 1 h in 2×blocking solution (Boehringer Mannheim, cat. no. 1585762) containing 1×maleic acid buffer (Boehringer Mannheim, cat. no.1585762).

Anti-DIG antibody labelled with alkaline phosphatase (Boehringer Mannheim, cat. no. 1093274) was added to the blocking solution at a concentration of 0.075 units/ml and rotary incubation continued for a further 30 min.

The membrane was then washed for 2×15 min in 1×wash buffer (Boehringer Mannheim, cat. no. 1585762) and transferred to 1×detection buffer (Boehringer Mannheim. cat. no. 1585762) for 5 min.

The chemiluminescent substrate CDP-Star (Boehringer Mannheim, cat. no. 1685627) was diluted 1:100 in detection buffer and 1 ml was added per 150 $cm^2$ of membrane. The substrate solution was spread evenly between clear transparency sheets and the signal was detected at room temperature using X-ray film (AGFA Eurix RP1) with intensifying screens (Dupont Quanta III-T).

Differential intensity of hybridization to male and female DNA samples indicated probes derived from clones containing a male-associated fragment from RAPD PCR with each of primers OPAC.06, OPAD.11, OPAI.05 and OPAM.07 (data not shown). Attempts to recover a cloned male-associated fragment from RAPD PCR with primer OPAM.01 were unsuccessful.

Example 2

Sequence Analysis of Cloned Male-Associated Fragments

DNA sequencing was performed using dideoxy sequencing chemistry utilising the ABI PRISM™ Dye Terminator Cycle-Sequencing-Ready Reaction Kit (ABI Perkin-Elmer) with AmpliTaq DNA polymerase, according to the manufacturer's instructions (ABI Perkin-Elmer). Products of sequencing reactions were analysed according to the manufacturer's instructions on an ABI A373 sequencer at the University of Queensland DNA Sequence and Analysis Facility.

The sequence of cloned inserts of recombinant plasmids, derived from recovered products of RAPD PCR with each of primers OPAC.06, OPAD.11, OPAI.05 and OPAM.07, that hybridized differentially with male DNA on dot blots are shown in SEQ ID NOS: 1, 2, 3 and 4, respectively. These inserts are known henceforth as EY.AC6, EY.AD11, EY.AI5 and EY.AM7, respectively.

Hybridization Analysis of Cloned Male-Associated Fragments

Samples of genomic DNA (2.5 μg) from nine male and nine female horses were digested with 5 units of Sau3AI (New England BioLabs) in NEBuffer (New England BioLabs: 100 mM NaCl, 10 mM bis-tris-propane-HCl, pH 7.0 at 25° C., 10 mM $MgCl_2$, 1 mM, dithiothreitol) and 0.1 mg/ml BSA in a final volume of 25 μl.

The digested samples, together with a DIG-labelled DNA molecular weight marker mix (Boehringer Mannheim. cat. no. 1218603), were electrophoresed in 1% (w/v) agarose at 70V for 3 h in 0.5×TBE. Resolved fragments were capillary-transferred overnight in 0.4M NaOH to a positively-charged nylon membrane (Boehringer Mannheim; 30). Following transfer, the membrane was neutralised with 3×10 min washes in 2×SSC. All hybridizations were performed according to the DIG System User's Guide for Filter Hybridization (Boehringer Mannheim).

Membranes were prehybridized at 50° C. for at least 2 h in 10 ml of DIG Easy Hyb hybridization buffer (Boehringer Mannheim. cat. no. 1603558) in glass hybridization bottles (Hybaid) placed in a Eurotherm 91E Rotating Hybridization Incubator (Model 310: Robbins Scientific).

DIG-labelled DNA probes were prepared as described above from the four recombinant plasmids containing inserts EY.AC6, EY.AD11, EY.AI5 and EY.AM7. Each was added to 4 ml of DIG Easy Hyb solution (Boehringer Mannheim)

at a concentration of 50–100 ng/ml and denatured at 68° C. for 10 min. The prehybridization solution was replaced by the probe solution and hybridization was conducted in the rotating incubator at 50° C. for 14–16 h.

The membrane was then removed and washed for 3×10 min at low stringency (2×SSC, 0.1% (w/v) SDS, 25° C.) followed by 2×10 min at high stringency (0.2×SSC, 0.1% (w/v) SDS, 68° C.). The washed membrane was rotary-incubated for 1 h in 2×blocking solution (Boehringer Mannheim, cat. no. 1585762) containing 1×maleic acid buffer (Boehringer Mannheim, cat. no. 1585762).

Anti-DIG antibody labelled with alkaline phosphatase (Boehringer Mannheim, cat. no. 1093274) was added to the blocking solution at a concentration of 0.075 units/ml and rotary incubation continued for a further 30 min.

The membrane was then washed for 2×15 min in 1×wash buffer (Boehringer Mannheim, cat. no. 1585762) and transferred to 1×detection buffer (Boehringer Mannheim, cat. no. 1585762) for 5 min. The chemiluminescent substrate CDP-Star (Boehringer Mannheim, cat. no. 1685627) was diluted 1:100 in detection buffer and 1 ml was added per 150 $cm^2$ of membrane. The substrate solution was spread evenly between clear transparency sheets and the signal was detected at room temperature using X-ray film (AGFA Eurix RP1) with intensifying screens (Dupont Quanta III-T).

The male-differential hybridization pattern using EY.AI5 indicated that this sequence is present in multiple copies in the DNA of all male horses surveyed. A homologous sequence is present in the female genome but is much less abundant, where the relative intensity and pattern of hybridization are suggestive of just one or a few copies.

In order to confirm that the cloned fragment EY.AI5 represents a canonical genomic repeated element, a DIG-labelled probe was prepared by direct PCR of male genomic DNA using primers EQYL2: 5'-AGCGGAGAAAGGAATCTCTGG-3' (SEQ ID NO: 12) and EQYR4: 5'-TTCGTCCTCTATGTTGAAATCAG-3' (SEQ ID NO: 14) derived from the sequence of EY.AI5 (nts 6–26 and the reverse complement of nts 173–195, respectively, in SEQ ID NO: 3; both primers provided by Bresatec Custom Oligos).

The hybridization patterns with both probes are similar, although the direct genomic probe appeared to hybridize relatively more strongly with fragments smaller than 900 bp in both male and female DNA, suggesting that genomic representatives of the repeat include sequences that are not part of the cloned EY.AI5 fragment.

The four cloned sequences EY.AC6, EY.AD11, EY.AI5 and EY.AM7 were subsequently DIG-labelled and hybridized with Southern blots of male and female genomic DNA that had been digested with nine different restriction enzymes. All showed male-specific hybridization patterns but also hybridized with female DNA, albeit to a significantly lesser extent.

These data demonstrate that each of the four sequences is repeated many times in the male genome and hence, by comparison with hybridization to female DNA, on the Y chromosome.

The striking similarity of hybridization patterns with all four probes to fragments cut by restriction enzymes having a six-base recognition sequence (KpnI, EcoRI, HindIII, BamHI) implies that all four cloned fragments are components of a single long-range tandem repeat in the equine Y chromosome. Sequence analysis of the four cloned fragments revealed overlap between EY.AC6 and EY.AM7 (SEQ ID NOS: 1 and 4), consistent with this interpretation.

Of the four cloned sequences, EY.AI5 showed the greatest quantitative difference between male and female DNA. Restriction patterns suggest that it has a basic repeat unit in the genome of approximately 230 bp (TaqI and RsaI digests), consistent with the length of the sequenced isolate (SEQ ID NO: 3).

Figure 1:
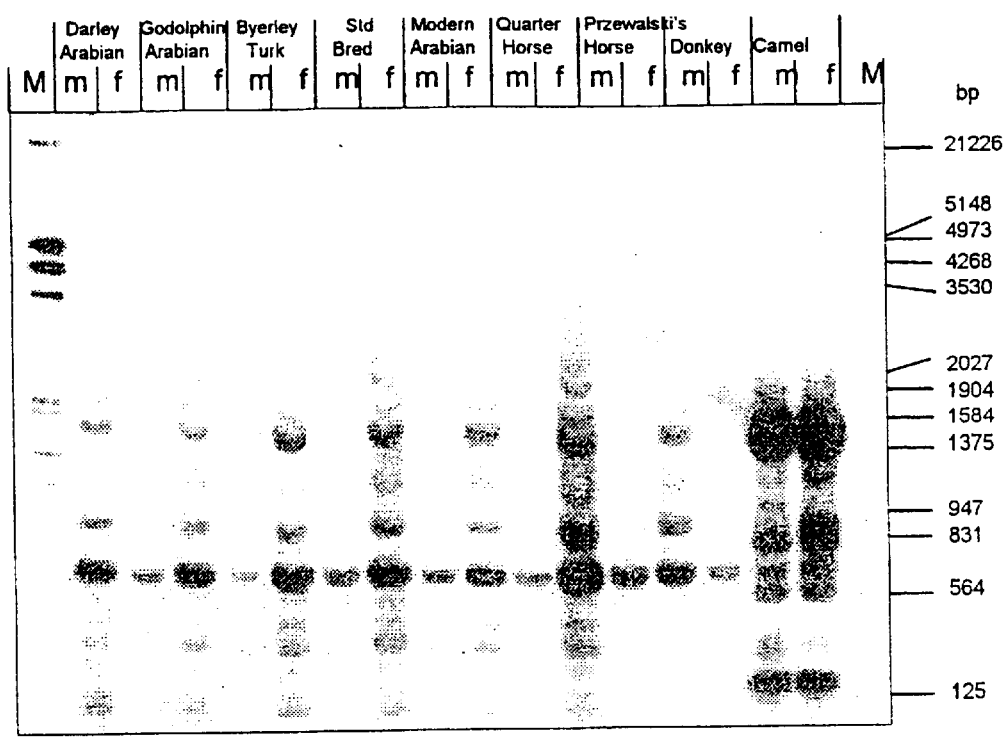
FIG. 1 shows hybridization analysis of horse breeds, donkey and camel with male-associated sequence EY.AI5. Samples of genomic DNA (2.5 μg) from male (m) and female (f) horses of various breeds (Family Equidae: *Equus caballus*) as well as Przewalski's horse (*E. przewalskii*), donkey (*E. asinus*) and the camel (Family Camelidae: *Camelus dromedarius*) as indicated, were digested with Sau3AI. The fragments were resolved by agarose gel electrophoresis, transferred onto positively-charged nylon membrane and hybridized with digoxigenin-labelled probe EY.AI5, as described in the text. The lane labelled M contained DNA standards whose sizes are indicated in base pairs.

Using the conditions described above, the cloned sequence EY.AI5 was DIG-labelled and hybridized with Southern blots of male and female genomic DNA that had been isolated from a variety of horse breeds and digested with Sau3AI (FIG. 1). Hybridization patterns were similar for all breeds examined, including the subspecies known as Przewalski's horse. This confirms the sex-differential occurrence of EY.AI5 sequences throughout the species *Equus caballus*.

Example 3

Conceptual Basis for Discriminatory PCR-Based Sexing Assay

Each of the four male-associated DNA sequences is clearly present in the equine Y chromosome since each shows a male-specific hybridization pattern, but none is unique to the male genome. Considering the four candidates as targets for a diagnostic test for the equine Y chromosome, the EY.AI5 fragment appears to offer most promise in that it shows the greatest differential between abundance on the Y chromosome and elsewhere. Accordingly, further studies focused on this sequence in an attempt to develop PCR conditions that would provide absolute discrimination between male and female equine DNA by utilising potential differences between the sequence on the Y chromosome and its homologue(s) elsewhere in the genome.

The fact that the EY.AI5 sequence is repeated on the Y chromosome implies that it is not represented by a single, definable sequence; repeated DNA elements invariably show sequence heterogeneity (e.g. 60). Cloning of PCR-amplified sequences yields single, specific representatives that, in addition to intrinsic sequence variations, may additionally contain errors due to incidental in vitro and in vivo mutagenesis.

Furthermore, EY.AI5-primed sequence(s) present in female genomes must be analysed to allow identification of possible sequence differences between it/them and Y-chromosomal representatives.

Analysis of EY.AI5 Sequences in Male and Female Genomic DNA

For the above reasons, samples of genomic DNA from individual male and female horses were amplified by PCR from a pair of primers specific to the sequence EY.AI5. Primers EQYL1: 5'-GTCGTAGCGGAGAAAGGAATC-3' (SEQ ID NO: 15) and EQYR1: 5'-AGCGGACTGTTCCGTTTCGG-3' (SEQ ID NO: 16) derived from the sequence of EY.AI5 (nts 1–21 and the reverse complement of nts 206–225, respectively, in SEQ ID NO: 3) were used to amplify genomic DNA targets from a male and female horse (both primers provided by Bresatec Custom Oligos). The products were sequenced directly from these primers, without cloning, to allow sequence analysis of the bulk population of repeated elements.

The sequence data (FIG. 2) show minor variations between the individual (cloned) representative EY.AI5 and the bulk sequence population in the male.

Two regions in fragments derived directly from the male genome differ from the equivalent regions in female-derived fragments (nts 1–30 and nts 162–220). These regions of sequence divergence were chosen as the annealing targets for PCR primers designed to discriminate between EY.AI5 sequences in male and female genomic DNA.

Example 4
Development of PCR-Based Equine Sexing Assay

A primer pair was derived from the sequence data of FIG. 2 for specific detection of equine Y-chromosomal DNA. These primers are EQYL2: 5'-AGCGGAGAAAGGAATCTCTGG3' (SEQ ID NO: 12) and EQYR5: 5'-TACCTAGCGCTTCGTCCTCTAT-3' (SEQ ID NO: 13), derived from nts 6–26 and the reverse complement of nts 184–205, respectively, of the male genomic DNA sequence shown in FIG. 2 (underlined). These two regions exhibit significant sequence differences between male and female genomes.

Amplification of equine genomic DNA samples (15 pg to 2 ng) from these primers (both primers provided by Bresatec Custom Oligos) yielded a product of approximately 200 bp from male DNA samples and no detectable product from female DNA samples (data not shown). Analysis of genomic DNA samples from ten unrelated horses (data not shown) confirmed that PCR amplification from these primers provides an accurate means of detecting the presence of Y-chromosomal DNA sequences.

In a diagnostic assay for genetic sex, no detectable product of PCR amplification from male-specific primers may result not only from a female sample but from PCR failure or loss of sample. The possibility of false negative results must be minimised. For this reason, a duplex PCR assay was developed in which a 121 bp (approximately) fragment of a dispersed autosomal repeated sequence (SINE; 61) was amplified simultaneously with the Y-specific target.

Primers used to amplify the SINE element were EQSIN8: 5'-GCCCAGTGTTTCGTTGGTTCG-3' (SEQ ID NO: 17) and EQSIN9: 5'-CATAGTTGTATATTCTTCGTTGTGG-3' (SEQ ID NO: 18), derived from nts 53–72 and the reverse complement of nts 148–172, respectively, of the ERE-1 SINE sequence family (61).

Duplex PCR amplifications were mutually optimised by inclusion of a common ml3 sequence at the 5'-termini of all four primers (62.63). The two primer pairs used for duplex equine sexing by PCR were:

sexing primers:
mEQYL2 5'-GCGGTCCCAAAAGGGTCAGTA-GCGGAGAAAGGAATCTCTGG-3' (SEQ ID NO: 19)
mEQYR5 5'-GCGGTCCCAAAAGGGTCAGTT-ACCTAGCGCTTCGTCCTCTAT-3' (SEQ ID NO: 20)
control primers:
mEQSIN8 5'-GCGGTCCCAAAAGGGTCAGTG-CCCAGTGTTTCGTTGGTTCG-3' (SEQ ID NO: 21)
mEQSIN9 5'-GCGGTCCCAAAAGGGTCAGT-CATAGTTGTATATTCTTCGTTGTGG-3' (SEQ ID NO: 22)

Duplex PCR reactions for internally-controlled assay of equine genetic sex were conducted in plastic capillary tubes (for use with the Corbett Research FT'S-1 thermal cycler) containing 50 mM KCl, 10 mM Tris-HCl, pH 8.3, 0.001% (w/v) gelatin, 2 mM $MgCl_2$, 100 $\mu$M dATP, 100 $\mu$M dCTP, 100 $\mu$M dGTP, 100 $\mu$M dTTP, 0.2 $\mu$M mEQSIN8, 0.2 $\mu$M mEQSIN9, 0.45 $\mu$M mEQYL2, 0.45 $\mu$M mEQYR5 (all four primers provided by Bresatec Custom Oligos) and 0.5 units of AmpliTaq (Perkin-Elmer) in a total volume of 10 $\mu$l.

Samples were placed in a Corbett Research FTS-1 capillary thermal cycler and subjected to a heating program of 94° C. for 30 sec, 69° C. for 30 sec and 72° C. for 30 sec for a total of six cycles, followed by an additional 20 cycles of 94° C. for 30 sec and 72° C. for 30 sec, then finally held at 25° C. pending analysis by agarose gel electrophoresis.

The products were electrophoresed in 2% (w/v) agarose gel in TAE buffer (Boehringer Mannheim) at 100V for approximately 30 min, then stained with ethidium bromide and visualised under uv irradiation. Duplex PCR amplification of equine genomic DNA samples resulted in a single visible fragment of approximately 160 bp from female horse DNA, resulting from amplification of SINE elements. Male DNA gave rise to a similar band and an additional band at approximately 240 bp, resulting from amplification of Y-chromosomal EY.AI5 elements. No product was seen in the absence of DNA.

The duplex PCR sexing assay described above is clearly able to identify and discriminate between male and female DNA samples, from 5 ng to as little as 20 pg (approximately equivalent to the amount of DNA in three cells).

Example 5
Application of Duplex PCR Sexing Assay to Horses of Various Breeds Samples of DNA isolated from male and female horses of various breeds were analysed by duplex PCR as described above.

Duplex PCR with the sexing and control primers was able to identify and discriminate between DNA samples from male and female horses of all breeds, with similar results for all breeds including the subspecies known as Przewalski's horse.

Example 6
Application of Duplex PCR Sexing Assay to Whole Blood Cells

The preceding examples illustrate successful application of the described duplex PCR sexing assay to small DNA samples. For ease of utility it is desirable to conduct the assay on small numbers of cells without the necessity to isolate DNA from them. White blood cells were used to establish appropriate assay conditions.

Blood samples were withdrawn into Vacutainer® CPT™ tubes with sodium citrate (Becton Dickinson). Tubes were kept upright at room temperature and processed within 2 hours of collection.

Each tube was centrifuged in a swinging bucket rotor (Sigma 3K18 with 11133 rotor) at 1900 g for 30 min at 24° C. Approximately 60–70% of the clear plasma layer was removed then the remaining liquid above the gel matrix, substantially free of red blood cells, was transferred into a clean tube. The sample was diluted to 10 ml with PBS and centrifuged at 300×g for 15 min at 24° C. Supernatant was removed and the pellet resuspended gently in 10 ml of PBS and centrifuged under the same conditions. The pellet was again suspended in 10 ml of PBS then centrifuged at 100×g.

The cell pellet was resuspended in 250 $\mu$l of PBS and the suspension counted by haemocytometer to determine the concentration of nucleated cells. The suspension was finally diluted in PBS to a concentration of $10^6$ nucleated cells/ml.

Samples of cell suspensions from male and female horses were serially diluted in PBRS containing 50 mM DTT and appropriate dilutions were subjected to two successive freeze/thaw cycles: tubes containing the samples were initially floated on liquid nitrogen for 1–2 min until frozen, then transferred to a water bath at room temperature until the suspension thawed. The tubes were placed in a boiling water bath for 15 min then cooled on ice. Duplex PCR reactions were conducted in plastic capillary tubes (for use with the Corbett Research FTS-1 thermal cycler) containing 50 mM KCl, 10 mM Tris-HCl, pH 8.3, 0.001%(w/v) gelatin, 2mM $MgCl_2$, 100 $\mu$M dATP, 100 $\mu$M dCTP, 100 $\mu$M dGTP, 100 $\mu$M dTTP, 0.2 $\mu$M mEQSIN8, 0.2 $\mu$M mEQSIN9, 0.45 $\mu$M mEQYL2, 0.45 $\mu$M mEQYR5, 0.5 units of AmpliTaq and 2 $\mu$l of treated cell suspension in a total volume of 10 $\mu$l.

Samples were placed in a Corbett Research FTS-1 capillary thermal cycler and subjected to a heating program of 94° C. for 30 sec. 69° C. for 30 sec and 72° C. for 30 sec for a total of six cycles, followed by an additional 21 cycles of 94° C. for 30 sec and 72° C. for 30 sec, then finally held at 25° C. pending analysis by agarose gel electrophoresis.

The products were electrophoresed in 2% (w/v) agarose gel in TAE buffer (Boehringer Mannheim) at 100V for approximately 30 min, then stained with ethidium bromide and visualised under uv irradiation.

As before, no bands were observed in the absence of equine DNA whereas bands are clearly visible with 20 pg of DNA from a female horse (single band at approximately 160 bp) and a male horse (two bands, at approximately 160 bp and 240 bp).

Samples of white blood cells containing approximately 5 cells to 100 cells each yielded one (160 bp) or two (160 and 240 bp) bands, consistent with their origin from female or male horses, respectively.

Example 7

Application of Duplex PCR Sexing Assay to Equine Embryos

Eight embryos were recovered from five mares approximately eight days after fertilisation and each was immediately split into four or more sections depending on the size of the blastocyst (each sample contained an estimated maximum of 50 cells). Splitting was performed by micromanipulation (1,2) in 50 µl of PBS. Each section of the blastocyst was collected with 2 µl of 4% (w/v) BSA (Miles Pentex crystalline, cat. no. 81-001-4; 1,2) and transferred into 7.5 µl of deionised water. The sections were stored frozen at −20° C.

The thawed suspension of each embryo section, containing approximately 15–50 cells, was made 20 mM in DTT and dispensed randomly into tubes numbered from 8 to 39. The 32 samples were from this stage processed 'blind' by a second individual who had not been involved with embryo collection, splitting or sample preparation.

Each sample was subjected to two successive freeze/thaw cycles. For each cycle the tubes containing the samples were floated on liquid nitrogen for 1–2 min until frozen, then transferred to a water bath at room temperature until the suspension thawed. The tubes were finally placed in a boiling water bath for 15 min then cooled on ice.

Duplex PCR reactions were conducted in plastic capillary tubes (for use with the Corbett Research FTS-1 thermal cycler) containing 50 mM KCl, 10 mM Tris-HCl, pH 8.3, 0.001%(w/v) gelatin, 2 mM MgCl$_2$, 100 µM dATP, 100 µM dCTP, 100 µM dGTP, 100 µM dTTP, 0.2 µM mEQSIN8, 0.2 µM mEQSIN9, 0.6 µM mEQYL2, 0.6 µM mEQYR5, 0.5 units of AmpliTaq and 9.5 µl of embryo cell suspension in a total volume of 20 µl.

Samples were placed in a Corbett Research FTS-1 capillary thermal cycler and subjected to a heating program of 94° C. for 30 sec, 69° C. for 30 sec and 72° C. for 30 sec for a total of six cycles, followed by an additional 21 cycles of 94° C. for 30 sec and 72° C. for 30 sec, then finally held at 25° C. pending analysis by agarose gel electrophoresis.

The products were electrophoresed in 2% (w/v) agarose gel in TAE buffer (Boehringer Mannheim) at 100V for approximately 30 min, then stained with ethidium bromide and visualised under uv irradiation.

No bands are observed in the absence of equine DNA whereas bands are clearly visible with 20 pg of DNA from female DNA (single band at approximately 160 bp) and male DNA (two bands, at approximately 160 bp and 240 bp). Bands are clearly visible with both 125 and 5 (approximately) white blood cells from a female horse (single band at approximately 160 bp) and a male horse (two bands, at approximately 160 bp and 240 bp).

Products resulting from assay of embryo sections showed relatively weak signals which were variable in intensity; this was found subsequently to result from sub-optimal PCR conditions due to a pH shift caused by the BSA used in the collection of embryo sections.

Two individuals, who had not been involved in earlier stages of the analysis, independently called the sex of each embryo section from the assay results. The calls of both individuals were in complete agreement and are shown in Table 1.

Table 1 shows the analysis of sex of embryo biopsies by duplex PCR. Embryos were recovered from mares approximately eight days after fertilisation, cut into four or more sections and the sections frozen at −20° C. The thawed sections, each containing approximately 15–50 cells, were dispensed randomly into tubes numbered from 8 to 39 and the 32 samples were analysed 'blind' by duplex PCR, as described in the text. At the conclusion of assay, two further individuals independently called the sex of each assay result. The calls of both individuals were in complete agreement. F is female diagnosis, M is male diagnosis and NR is no result. The data have been rearranged for clarity.

For every embryo, all four sections from the same embryo were called as the same sex, with the exception of sample 34 which yielded no result (neither male-specific band nor control band was visible, confirming the value of including primers for an internal control). The probability of such a result arising by chance is $<10^{-7}$.

These data provide statistical validation of the duplex PCR sexing assay for embryo sections.

TABLE 1

| Embryo no. | Estimated no. cells | Sample ID | Sex called |
| --- | --- | --- | --- |
| 1 | 50 | 12 | F |
| 1 | 50 | 39 | F |
| 1 | 50 | 20 | F |
| 1 | 50 | 33 | F |
| 2 | 45 | 10 | M |
| 2 | 45 | 13 | M |
| 2 | 45 | 30 | M |
| 2 | 35 | 24 | M |
| 3 | 30 | 31 | F |
| 3 | 35 | 17 | F |
| 3 | 45 | 37 | F |
| 3 | 35 | 19 | F |
| 4 | 50 | 36 | M |
| 4 | 50 | 8 | M |
| 4 | 50 | 21 | M |
| 4 | 50 | 38 | M |
| 5 | 50 | 27 | F |
| 5 | 30 | 16 | F |
| 5 | 50 | 35 | F |
| 5 | 50 | 29 | F |
| 6 | 50 | 25 | M |
| 6 | 50 | 14 | M |
| 6 | 50 | 23 | M |
| 6 | 50 | 11 | M |
| 7 | 50 | 32 | M |
| 7 | 50 | 28 | M |
| 7 | 50 | 9 | M |
| 7 | 50 | 22 | M |
| 8 | 15 | 26 | M |
| 8 | 25 | 18 | M |
| 8 | 40 | 15 | M |
| 8 | 40 | 34 | NR |

Example 8

Identification of Long-Range Repeat in the Equine Y Chromosome

To investigate the inter-relation, repetition, conservation and genomic environment of the four described sequence elements associated with the equine Y chromosome, these elements were used as probes to identify recombinant bacteriophage in an equine genomic library.

Equine Genomic Library

A male horse genomic DNA library in the Lambda Fix® II vector was obtained from Stratagene (cat. no. 946701). The estimated titre of the library after a single round of amplification was $2.0 \times 10^9$ plaque forming units (pfu)/ml. Phage and host bacteria were cultured according to methods detailed in the instruction manual provided with the library (Stratagene).

Screening of Equine Genomic Library with EY.AI5 Probe

For the first round of screening a total of 25,000 to 30,000 plaques grown in host E. coli XL1-Blue NIRA (P2) were present on each 150 mm plate of growth medium. Duplicate plaque lifts were made from each plate and DNA was bound to uncharged Nylon Membranes for Colony and Plaque Hybridization (132 mm diameter) purchased from Boehringer Mannheim (cat. no. 1699083) according to protocols outlined in the DIG System User's Guide for Filter Hybridization (Boehringer Mannheim). After uv cross-linking (Bio-Rad GS Gene Linker), membranes were prehybridized at 42° C. for at least 2 h in 10 ml of DIG Easy Hyb hybridization buffer (Boehringer Mannheim, cat. no. 1603558) in glass hybridization bottles (Hybaid) placed in a Eurotherm 91E Rotating Hybridization Incubator (Model 310: Robbins Scientific). A DIG-labelled EY.AI5 probe and a control probe for a 121 bp (approximately) fragment of a dispersed autosomal repeated sequence (SINE: 61) were prepared as described above from the inserts of recombinant plasmids, using the SP6 and T7 primers. Each was added to 10 ml of DIG Easy Hyb solution (Boehringer Mannheim) at a concentration of 25–50 ng/ml and denatured at 68° C. for 10 min. The prehybridization solution was replaced by the probe solution and hybridization was conducted in the rotating incubator at 42° C. for 14–16 h.

The membrane was then removed and washed for 3×10 min at low stringency (2×SSC, 0.1% (w/v) SDS, 25° C.) followed by 2×10 min at high stringency (0.2×SSC, 0.1% (w/v) SDS, 68° C.). The washed membrane was rotary-incubated for 1 h in 2×blocking solution (Boehringer Mannheim, cat. no. 1585762) containing 1×maleic acid buffer (Boehringer Mannheim, cat. no. 1585762).

Anti-DIG antibody labelled with alkaline phosphatase (Boehringer Mannheim, cat. no. 1093274) was added to the blocking solution at a concentration of 0.075 units/ml and rotary incubation continued for a further 30 min.

The membrane was then washed for 2×15 min in 1×wash buffer (Boehringer Mannheim, cat. no. 1585762) and transferred to 1×detection buffer (Boehringer Mannheim, cat. no. 1585762) for 5 min.

The chemiluminescent substrate CDP-Star (Boehringer Mannheim, cat. no. 1685627) was diluted 1:100 in detection buffer and 1 ml was added per 150 cm² of membrane. The substrate solution was spread evenly between clear transparency sheets and the signal was detected at room temperature using X-ray film (AGFA Eurix RP1) with intensifying screens (Dupont Quanta III-T).

Fifty plaques of the 100 (approximately) plaques that gave positive signals in duplicate were selected from the 300,000 that were screened and each was removed in a small agar plug; the plugs were stored in SMT buffer at 4° C.

A second round of screening was conducted at reduced plaque density (approx. 3.500 pfu) for 20 of the positives. Methods for plaque lifts and hybridizations were identical to those used in first round screening. Sixteen independent clones positive for EY.AI5 probe (on duplicate filters) were selected for further investigation. These were: 31.1, 31.2, 31.3. 31.4, 31.5 (originating from five positive plugs selected from plate number 31 in the first screening round). 32.3. 33.1. 33.2, 33.4, 34.1, 34.2, 34.3. 34.5, 36.1, 36.2 and 36.3 (similarly selected from plates 32, 33, 34 and 36. respectively).

Isolation of DNA from Recombinant Phage

DNA was isolated from five positive clones using host strain E. coli XL1-Blue NIRA growing at 37° C. overnight in 50 ml LB medium supplemented with 0.3% (v/v) glycerol and 10 mM MgSO4 (64). DNA (200 μg) was isolated using anion-exchange resin under appropriate salt and pH conditions (QIAGEN Lambda Maxi Kit; cat. no. 12562) in accordance with the methods supplied by the manufacturers.

Southern Hybridization of Phage Inserts with EY.AI5 and EY.AD11 Probes

Twenty μg of recombinant phage DNA was incubated overnight with 40 units of restriction enzyme EcoRI or HindIII. All restriction digests were carried out with enzymes supplied by Boehringer Mannheim or New England Biolabs in buffers as supplied by the manufacturers and in accordance with their instructions. Aliquots of 10 μg of digested DNA, together with a DIG-labelled DNA molecular weight marker mix (Boehringer Mannheim, cat. no. 1218603), were electrophoresed in 1% (w/v) agarose at 80V for 5 h in 0.5×TAE. Resolved fragments were capillary-transferred overnight in 0.4M NaOH to a positively-charged nylon membrane (Boehringer Mannheim; 30). Following transfer, the membrane was neutralised with 3×10 min washes in 2×SSC then DNA was uv cross-linked to the membrane (Bio-Rad GS Gene Linker).

All hybridizations were performed according to the DIG System User's Guide for Filter Hybridization (Boehringer Mannheim). Membranes were prehybridized at 42° C. for at least 2 h in 10 ml of DIG Easy Hyb hybridization buffer (Boehringer Mannheim. cat. no. 1603558) in glass hybridization bottles (Hybaid) placed in a Eurotherm 91E Rotating Hybridization Incubator (Model 310: Robbins Scientific).

DIG-labelled DNA probes were prepared as described above from the two recombinant plasmids containing inserts EY.AD11 and EY.AI5 (Example 2). Probe was added to 10 ml of DIG Easy Hyb solution (Boehringer Mannheim) at a concentration of 25–50 ng/ml and denatured at 68° C. for 10 min. The prehybridization solution was replaced by the probe solution and hybridization was conducted in the rotating incubator at 42° C. for 14–16 h.

The membrane was then removed and washed for 3×10 min at low stringency (2×SSC, 0.1% (w/v) SDS, 25° C.) followed by 2×10 min at high stringency (0.2×SSC, 0.1% (w/v) SDS, 68° C.). The washed membrane was rotary-incubated for 1 h in 2×blocking solution (Boehringer Mannheim. cat. no. 1585762) containing 1×maleic acid buffer (Boehringer Mannheim. cat. no. 1585762).

Anti-DIG antibody labelled with alkaline phosphatase (Boehringer Mannheim, cat. no. 1093274) was added to the blocking solution at a concentration of 0.075 units/ml and rotary incubation continued for a further 30 min.

The membrane was then washed for 2×15 min in 1×wash buffer (Boehringer Mannheim, cat. no. 1585762) and transferred to 1×detection buffer (Boehringer Mannheim, cat. no. 1585762) for 5 min.

The chemiluminescent substrate CDP-Star (Boehringer Mannheim, cat. no. 1685627) was diluted 1:100 in detection buffer and 1 ml was added per 150 cm² of membrane. The substrate solution was spread evenly between clear transparency sheets and the signal was detected at room temperature using X-ray film (AGFA Eurix RPl) with intensifying screens (Dupont Quanta III-T).

Following detection of the positive signals for EY.AI5 probe (FIG. 3a), the probe was stripped from the membrane by treatment with 0.1% (w/v) SDS in 0.2M NaOH at 68° C. for 20 min. The membrane was then hybridized using the methods detailed above with the probe for the EY.AD11 sequence (FIG. 3b). Most restriction fragments positive for EY.AI5 were also positive for EY.AD11. Phage 31.1 failed to exhibit hybridization with either probe.

Phage restriction fragments were selected for sequence analysis based on their hybridization to both probes. The fragments were alike in size to genomic repeated elements identified by using the same two probes for Southern analysis of equine genomic DNA digested with EcoRI and HindIII. Fragments selected for sequencing were: a 3.3 kb HindIII fragment from phage 33.1 (similar in size to a HindIII fragment in both male and female genomic DNA at an intensity ratio of approximately 2:1); a 4.4 kb HindIII fragment from phage 36.1 (similar in size to a HindIII fragment in both male and female genomic DNA at an intensity ratio of approximately 20:1); a 4.7 kb EcoRI fragment from phage 32.3 (similar in size to a genomic EcoRI band which hybridizes to both probes at low intensity in the male and at a barely detectable level in the female); and a 6.0 kb EcoRI fragment from phage 36.1 (present in male genomic DNA but not detected in the female).

Restriction Mapping of Recombinant Phage Inserts

Inserts of equine genomic DNA flanked by T3 and T7 promoter sites were excised from the Lambda Fix® II vector by digestion with NotI. This cassette (1 µg) was subjected to partial digestion with either EcoRI (for page 32.3 and 36.1) or HindIII (for phage 33.1 and 36.1). The partial digestion fragments, together with fragments of 1 DNA digested with HindIII and EcoRI as size markers (Boehringer Mannheim; cat. no. 528552), were electrophoresed through a 1% (w/v) agarose gel at 80V for 5 h in 0.5×TAE with ethidium bromide; the gel was then overlaid with a scale ruler and photographed with uv transillumination (302 nm).

The resolved fragments were transferred to an uncharged membrane (Hybond-N, Amersham cat. no. RPN303N) with 20×SSC following depurination in 0.25M HCl, denaturation in 0.5M NaOH, 1.5M NaCl and neutralization in 1M Tris (pH 7.5), 1.5M NaCl (65). The membranes were probed successively with biotinylated oligonucleotide probes for the T3 and T7 promoter sequences, respectively (New England Biolabs cat. nos. 1227-BT and 1223-BT); membranes were stripped before the second hybridization by treatment with 0.1% (w/v) SDS in 0.2M NaOH at 68° C. for 20 min. Prehybridization was done in glass hybridization bottles (Hybaid) placed in a Eurothermi 91E Rotating Hybridization Incubator (Model 310: Robbins Scientific) in 10 ml phosphate buffered 7% (w/v) SDS solution with 1% (w/v) BSA and 0.5 mg/ml carrier DNA (28). Biotinylated oligonucleotide probe was added to a final concentration of 10 ng/ml. Hybridization temperatures were 59° C. for the T7 probe and 49° C. for the T3 probe. Post-hybridization washes were in 5×SSC, 0.1% (w/v) SDS at 25° C. for 15 min, then in 5×SSC. 0.1% (w/v) SDS at 60° C. for 15 min. membranes were blocked with 10 ml of 1×Blocker (5.0% (w/v) SDS, 125 mM NaCl. 25 mM sodium phosphate (pH 7.2)) at 25° C. for 15 min. Alkaline phosphatase-conjugated streptavidin (Boehringer Mannheim: cat no. 1093266) was added to the blocking mixture to a concentration of 1 unit/ml and the membranes were treated for a further 10 min. Post-treatment washes were in 1×Blocker for 10 min then in two changes of 0.1×Blocker for 15 min followed by detection with CDP-Star and autoradiography as outlined above.

Sizes of hybridizing fragments were estimated by comparison with positions of control size markers run concurrently in the gel. The resulting ladder of DNA fragments corresponded to the distance from the T3 or T7 promoter site, respectively, and successive restriction sites (analagous to the ladder generated from labelled primers with dideoxy DNA sequencing). Because the T3 and T7 promoter sites flank the two ends of the insert, complementary maps were obtained, allowing confirmation of the position of restriction sites.

Analysis of complete digestion products on an ethidium bromide-stained gel provided additional information regarding distances separating all adjacent cleavage sites. Restriction maps of phage clones 32.3 (EcoRI), 33.1 (HindIII) and 36.1 (HindIII and EcoRI) are shown in FIGS. 4a, 5a and 6a, respectively.

Subcloning of Restriction Fragments from Recombinant Phage

Recombinant phage DNA (7.5 µg) was digested with 20 units of EcoRI (for phage 32.2 and 36.1) or HindIII (for phage 33.1 and 36.1) for 6 h at 37° C. Restriction fragments were resolved by electrophoresis in 1% (w/v) agarose in 0.5×TAE buffer containing ethidium bromide. Bands were visualized with uv transillumination (302 nm) and the selected fragments were excised. DNA was recovered using silica-gel membrane technology (QIAquick Gel Extraction Kit; QIAGEN cat. no. 28704) in accordance with the manufacturer s instructions.

The cloning vector was phagemid pBluescript® II KS+ (Stratagene) which had been linearized by digestion with either HindIII or EcoRI then treated with shrimp alkaline phosphatase (Boehringer Mannheim; cat. no. 1758250). Vector DNA was purified as above by gel electrophoresis and the QIAquick gel extraction technique. The linear vector (approx. 20 ng) and phage restriction fragments (approx. 20 ng) were ligated with 1 Weiss unit of T4 DNA ligase (Boehringer Mannheim) in 10 µl of T4 DNA ligase buffer, as supplied with the enzyme, at 15° C. for 16 h. Ligation reactions were used to transform 100 µl of competent E. coli DH5 a cells.

Single colonies of E.coli strain DH5 a were inoculated into 250 ml of LB broth and grown in a shaking incubator at 37° C. to an optical absorbance of approx. 0.5 at 550 nm. The cells were collected by centrifugation at 3.000 rpm for 5 min at 4° C. in an Eppendorf 5414C microcentrifuge. resuspended in 30 ml of cold 0.1M $MgCl_2$ and placed on ice for 20 min. The cells were collected by centrifugation as before and the pellet suspended in 1 ml of cold 0.1M CaCl2. Glycerol was added to 15% (v/v) and the competent cells were stored at −70° C.

For transformation, a 100 µl aliquot of competent cells was thawed and mixed with 10 µl of ligation reaction, placed on ice for 30 min, heat-shocked at 42° C. for 2 min then returned to ice for 2 min. The transformed cells were allowed to recover by incubation at 37° C. for 1 h in 900 µl of SOC medium (2% (w/v) bacto-tryptone, 0.5% (w/v) bacto-yeast extract, 10M NaCl, 2.5 mM KCl, 10 mM $MgCl_2$, 10 mM MgSO4, 20 mM glucose) and were then plated onto LB agar containing ampicillin (100 µg/ml) for overnight culture at 37° C. Eight or sixteen colonies were selected from ligations of each vector/insert pair.

A volume of 3 ml of LB broth containing ampicillin (100 µg/ml) was inoculated with each colony and bacterial suspensions were harvested after 16 h at 37° C. in a shaking incubator. Miniprep DNA was prepared from each suspension (Wizard™ Plus Minpreps, Promega cat no. A7500). Purified plasmid DNA was compared with uncut vector by gel electrophoresis to identify clones with plasmids containing an insert of appropriate size.

DNA from these clones was digested with either HindIII or EcoRI, as appropriate, and clones with excisable inserts of the correct size were used for sequence analysis. Insert-containing plasmid clones were as follows: 32.3E1 and 32.3E5 (pBluescript® II with 4.7 kb EcoRI fragments from recombinant phage 32.3); 33.1H2, 33.1H3, 33.1H4, 33.1H6, 33.1H7 and 33.1H8 (pBluescript® II with 3.3 kb HindIII fragments from recombinant phage 33.1); 36.1H1, 36.1H2, 36.1H4, 36.1H6, 36.1H7, 36.1H8, 36.1H9 and 36.1H10 (pBluescript® II with 4.4 kb HindIII fragments from recombinant phage 36.1): and 36.1E2 and 36.1E8 (pBluescrip® II with 6.0 kb EcoRI fragments from recombinant phage 36.1).

Single colonies of E.coli DH5a with plasmids 32.3E5, 33.1H2, 33.1H7, 36.1H7, 36.1H1 and 36.1E2 were used to prepare bacterial suspensions in 50 ml LB broth with ampicillin (100 µg/ml). Preparations of 100–200 µg of plasmid DNA were purified from these suspensions according to supplier's instructions using a QIAGEN Plasmid Kit and QIAGEN-tip 100 resin columns (QIAGEN; cat. no. 12144).

Sequence Analysis of Subcloned Phase Fragments Hybridizing to Probes EY.AI5 and EY.AD11

DNA sequencing was performed using dideoxy sequencing chemistry utilising the ABI PRISM™ BigDye Terminator Cycle Sequencing Ready Reaction Kit (ABI Perkin-Elmer) with AmpliTaq DNA polymerase according to the manufacturer's instructions (ABI Perkin-Elmer). Where apparent secondary DNA structure in insert 36.1H7 impeded the terminator sequencing reaction, the BigDye Primer Cycle Sequencing Ready Reaction Kit (T7) (ABI Perkin-Elmer) was used. Products of sequencing reactions were analysed according to the manufacturer's instructions on an ABI A377 sequencer at the Australian Genome Research Facility located at The University of Queensland.

A total of 112 sequencing reactions with an average read length of 700 bases were undertaken. Approximately 20 kb of novel equine genomic DNA sequences were recorded then analysed, firstly for homology to sequences described herein as EY.AC7, EY.AM17, EY.AD11 and EY.AI5, and secondly for homology to sequences available worldwide in GenBank (National Center for Biotechnology Information, Maryland, USA [NCBI]) and similar DNA and protein databases.

Primers for T3 and T7 promoter sequences flanking inserts in pBluescript® II vector (Bresatec Custom Oligos) were used for the initial sequencing, steps. Sequences were extended from their 3' extremity with 19–24-mer oligonucleotide primers (Bresatec Custom Oligos) designed for this purpose from known sequence data, then matching this extended sequence to the primary data. Replicate, overlapping and complementary strand sequencing assured the accuracy of the final genomic DNA sequences. Computer software used to construct contiguous DNA sequences was Sequencher™ 3.0 (Gene Codes Corporation) for Macintosh®.

Eight 4.4 kb HindIII fragments subcloned from phage 36.1 proved to be identical, differing only in the orientation of the insert in the vector. This conclusion was based on 100% identity observed within blocks of at least 400 bases of sequence. Application of this criterion established that the two 6.0 kb EcoRI fragments from phage 36.1 were also identical. Two subcloned EcoRI fragments of 4.7 kb from phage 32.3 were not identical.

Mapping and restriction analysis of phage clone 33.1 (see FIG. 5a) indicated the presence of two similar 3.3 kb HindIII fragments. Partial sequencing of six subcloned 3.3 kb inserts supported this view. Inserts in plasmids 33.1H7, 33.1H3, 33.1H4 and 33.1H6 were identical; inserts in plasmids 33.1H2 and 33.1H8 were identical to each other but exhibited 88–90% similarity with the former group. Accordingly, inserts in plasmids 33.1H7 and 33.1H2 were sequenced independently.

Figure 4B:
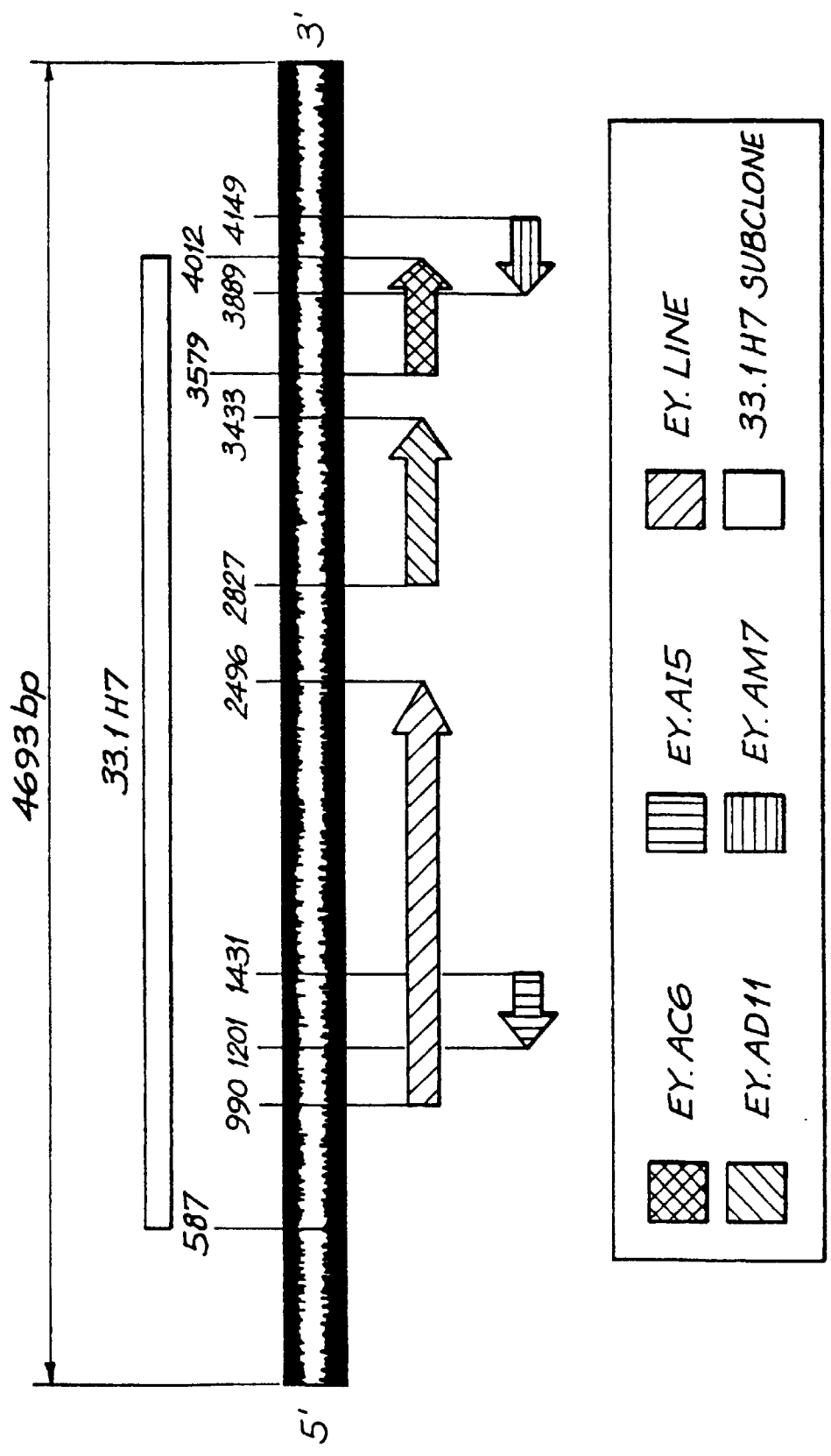
Figure 5B:
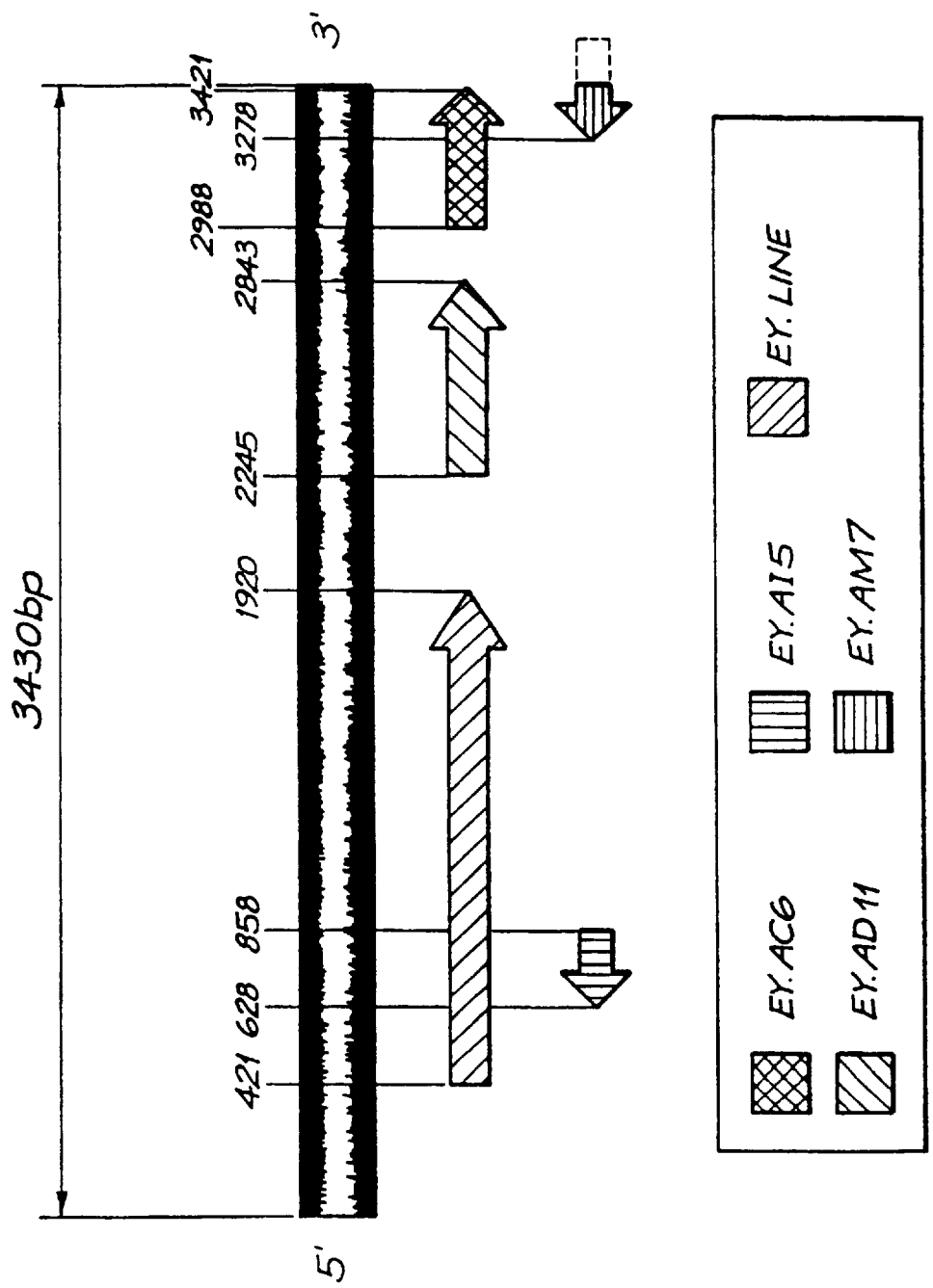
Figure 6B:
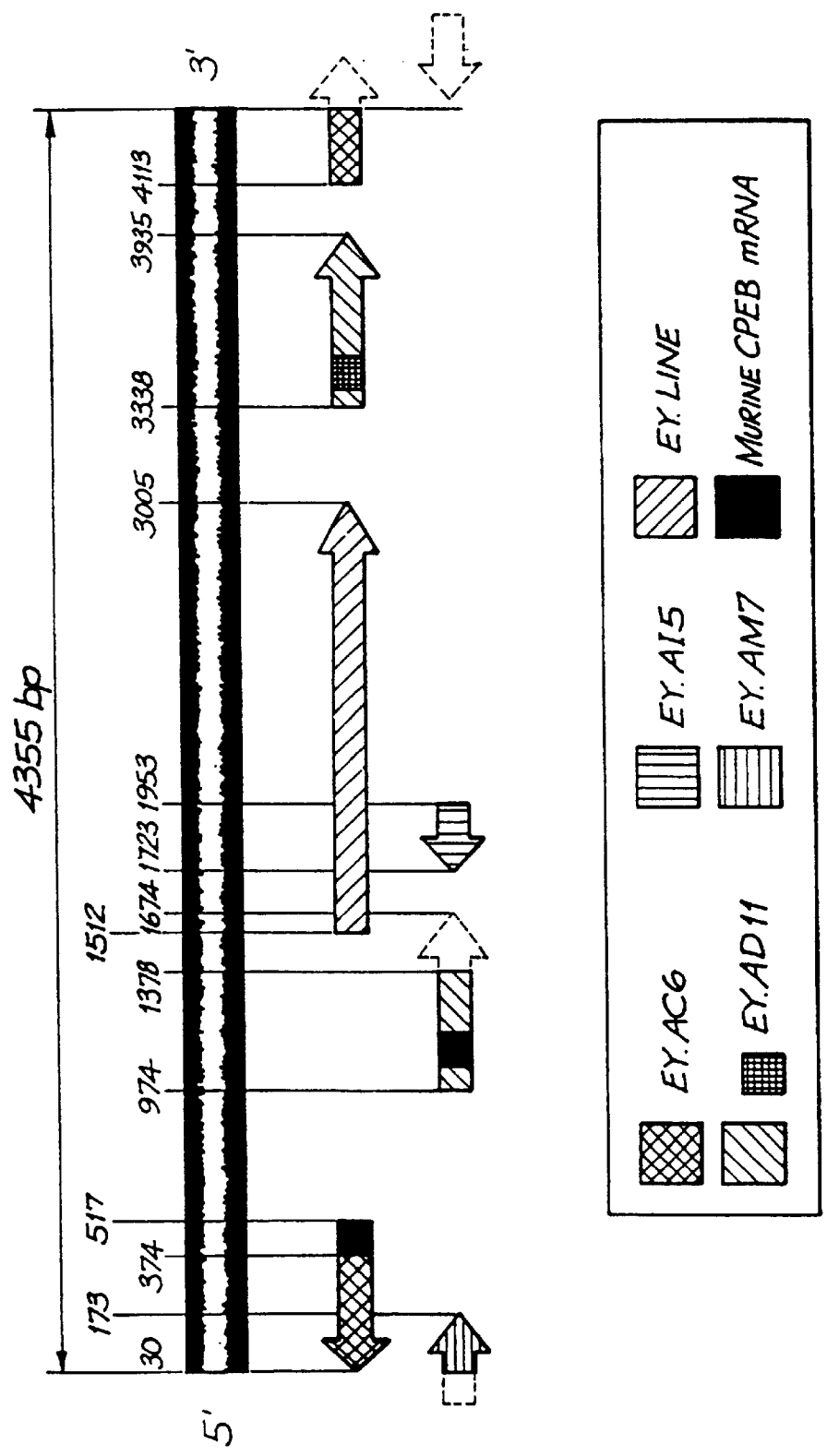

Sequencing of phage DNA selected for hybridization with EY.AI5 and EY.AD11 sequences (Example 2) revealed that these and the sequences EY.AC6 and EY.AM7 (Example 2) were components of a long range repeat unit in the equine Y chromosome. The structure of the repeat as it was found in equine genomic DNA inserts in phage 32.3, 33.1 (twice) and 36.1 is shown in FIGS. 4b, 5b and 6b.

Plasmid 32.3E1 contains an insert, possibly part of a pseudogene, with limited homology to open reading frames of a number of unrelated genes, as determined by a database nucleotide and protein translation search (GenBank BLAST 2.0; blastn and blastx programs; NCBI).

The repeat element identified in equine genomic DNA comprises sequences which include the aforementioned repeats EY.AI5, EY.AD11, EY.AC6 and EY.AM7. In addition, EY.AI5 sequence featured as part of a 1500 bp (approximately) unit, hereafter referred to as EY.LINE, found to be approximately 50% homologous at the protein level (GenBank BLAST 2.0; blastx search: NCBI) to regions of open reading frame 2 (ORF2) in a mammalian long interspersed repeated element (LINE: GenBank accession nos. U93574 (human) and AB012223 (dog)). These elements, when functional, are 6.0 kb in size and contain a 5' untranslated region (UTR) with an internal promoter, two open reading frames (ORF1 and ORF2) and a 3' UTR that terminates in a polyA tail. ORF1 encodes a nucleic acid binding protein and ORF2 encodes a protein with endonuclease and reverse transcriptase activities. The EY-LINE sequence is located at nucleotides 990–2497 of SEQ ID NO: 8, 421–1920 of SEQ ID NO. 9, 421–1930 of SEQ ID NO. 10. and 1502–2996 of SEQ ID NO. 11.

LINEs are highly repetitive DNA sequence elements capable of retrotransposition that pervade mammalian genomes. Most are functionally inactive due to truncations, rearrangements and nonsense mutations (67). LINEs are present in all mammals that have been studied (including marsupials) and are thought to be derived from a common ancestor. When cloned elements from a particular species are compared there may be differences between individual sequences. Southern hybridizations of restricted genomic DNA give species-specific patterns when hybridized with a LINE probe (68).

The aforementioned four DNA sequences associated with the equine Y chromosome, when used as probes, detect this EY.LINE repeated element. This element is, in turn, a part of a larger repeated element of 3.5 kb (minimum length) that is evident from comparison of FIGS. 4b, 5b and 6b. This explains the similarity between Southern hybridizations using the different sequences as probes. That the EY.LINE described here is specific to Equidae is illustrated by FIG. 1 where no hybridization of EY.AI5 is detected to restricted genomic DNA of the camel. The male specificity of EY.LINE in Equus spp. is illustrated clearly by the data of FIG. 1.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Herr, C., Holt, N., Pietrzak, U., Old, K. and Reed, K. (1990) Increased number of pregnancies per collected embryo by bisection of blastocyst stage ovine embryos. Theriogenology 33:244.
2. Herr, C. M. and Reed, K. C. (1991) Micromanipulation of bovine embryos for sex determination. Theriogenology 35:45–54.
3. Ford, C. E., Jones, K. W., Polani, P. E., de Almeida, J. C. and Briggs, J. H. (1959) A sex chromosome anomaly in a case of gonadal dysgenesis (Turner's syndrome). Lancet i:711–713.
4. Jacobs, P. A. and Strong, J. A. (1959) A case of human intersexuality having a possible XXY sex-determining mechanism. Nature 183:302–303.
5. Welshons, W. J. and Russell, L. B. (1959) The Y chromosome as the bearer of male determining factors in the mouse. Proc. Natl. Acad. Sci. USA 45:560–566.
6. Kent. M. G., Shoffner, R. N., Buoen, L. and Weber, A. F. (1986) XY sex-reversal syndrome in the domestic horse. Cytogenet. Cell Genet. 42:8–18.
7. Kent. M. G., Shoffner, R. N., Hunter, A., Elliston, K. O., Schroder, W., Tolley, E. and Wachtel, S. S. (1988) XY sex reversal syndrome in the mare: clinical and behavioral studies, H-Y phenotype. Hum. Genet. 79:321–328.
8. Nilliken, J. E., Paccamonti. D. L., Shoemaker, R. S. and Green. W. H. (1995) XX male pseudohermaphroditism in a horse. J. Am. Vet. Med. Assoc. 207:77–79.
9. Sinclair, A. H., Berta, P., Palmer, M. S., Hawkins. J. R., Griffiths. B. L., Smith. M. J., Foster, J. W., Frischauf, A.-M., Lovell-Badge, R. and Goodfellow. P. N. (1990) A gene from the human sex-determining region encoding a protein with homology to a conserved DNA-binding motif. Nature 346:240–244.
10. Koopman. P., Gubbay, J., Vivian. N., Goodfellow, P. and Lovell-Badge, R. (1991) Male development of chromosomally female mice transgenic for Sry. Nature 351:117–121.
11. Tiersch, T. R., Mlitchell, J. M. and Wachtel. S. S. (1991) Studies on the phylogenetic conservation of the SRYgene. Hum. Genet. 87:571–573.
12. Jost, A., Vigier, B., Prepin, J. and Perchellet, J. P. (1973) Studies on sex differentiation in mammals. Rec. Prog. Horm. Res. 29:1–41.
13. Pomp, D., Good, B. A., Geisert, R. D., Corbin, C. J. and Conley, A. J. (1995) Sex identification in mammals with polymerase chain reaction and its use to examine sex effects on diameter of day-10 or -11 pig embryos. J. Animal Sci. 73:1408–1415.
14. Peippo, J., Huhtinen, M. and Kotilainen, T. (1995) Sex diagnosis of equine preimplantation embryos using the polymerase chain reaction. Theriogenology 44:619–627.
15. Saiki, R. K., Scharf, S., Faloona, F., Mullis, K. B., Horn, G. T., Erlich, H. A. and Arnheim, N. (1985) Enzymatic amplification of b-globin genomic sequences and restriction site analysis for diagnosis of sickle cell anemia. Science 230:1350–1354.
16. Mullis, K., Faloona, F., Scharf, S., Saiki, R., Horn, G. and Erlich, H. (1986) Specific enzymatic amplification of DNA in vitro: the polymerase chain reaction. Cold Spr. Harb. Symp. Quant. Biol. 51:263–273.
17. Mardon, G., Mosher, R., Disteche, C. M., Nishioka, Y., McLaren, A. and Page, D. C. (1989) Duplication, deletion, and polymorphism in the sex-determining region of the mouse Y chromosome. Science 243:78–80.
18. Reed, K. C., Matthews, M. E. and Jones, M. A. S. (1986) Sex determination in ruminants using Y-chromosome specific polynucleotides. PCT AU87/00254, WO88/01300.
19. Reed. K. C., Lord, E. A., Matthaei, K. I., Mann. D. A., Beaton, S., Herr, C. M. and Matthews, M. E. (1988) Determination of genetic sex in ruminants using Y-chromosome-specific polynucleotides. PCT AU89/00029, WO89/07154.
20. Kent. M. G., Elliston, K. O., Shroeder, W., Guise, K. S. and Wachtel, S. S. (1988) Conserved repetitive DNA sequences (Bkrn) in normal equine males and sex-reversed females detected by in situ hybridization. Cytogenet. Cell Genet. 48:99–102.
21. Singh. L., Purdoni, I. F. and Jones, K. W. (1981) Conserved sex-chromosome-associated nucleotide sequences in eukaryotes. Cold Spr. Harb. Symp. Quant. Biol. 46:805–814.
22. Epplen, J. T., NicCarrey, J. R., Sutou, S. and Ohno, S. (1982) Base sequence of a cloned snake W-chromosome DNA fragment and identification of a male-specific putative mlRNA in the mouse. Proc. Natl. Acad. Sci. USA 79:3798–3802.
23. Miklos, G. L. G., Matthaei, K. I. and Reed, K. C. (1989) Occurrence of the $(GATA)_n$ sequences in vertebrate and invertebrate genomes. Chromosoma 98:194–200.
24. Levin, I., Crittenden, L. B. and Dodgson, J. B. (1993) Genetic map of the chicken Z chromosome using random amplified polymorphic DNA (RAPD) markers. Genomics 16:224–230.
25. Antoniou, E. and Skidmore, C. J. (1995) A bovine Y-specific marker amplified by RAPD. Animal Genet. 26:444–445.
26. Cushwa, W. T., Dodds, K. G., Crawford, A. M. and Medrano, J. F. (1996) Identification and genetic mapping of random amplified polymorphic DNA (RAPD) markers to the sheep genome. Mamm. Genome 7:580–585.
27. Amasino, R. M. (1986) Acceleration of nucleic acid hybridization rate by polyethylene glycol. Anal. Biochem. 152:304–307.
28. Church, G. M. and Gilbert, W. (1984) Genomic sequencing. Proc. Natl. Acad. Sci. USA 81:1991–1995.
29. Johnson, D. A., Gautsch, J. W., Sportsman, J. R. and Elder, J. H. (1984) Improved technique utilizing nonfat dry milk for analysis of proteins and nucleic acids transferred to nitrocellulose. Gene Anal. Techn. 1:3–8.
30. Reed, K. C. and Mann, D. A. (1985) Rapid transfer of DNA from agarose gels to nylon membranes. Nucl. Acids Res. 13:7207–7221.
31. Casey, J. and Davison. N. (1977) Rates of formation and thermal stabilities of RNA:DNA and DNA:DNA duplexes at high concentrations of formamide. Nucl. Acids Res. 4:1539–1552.
32. Denhardt. D. T. (1966) A membrane-filter technique for the detection of complementary DNA. Biochem. Biophys. Res. Commun. 23:641–646.
33. Wahl, G. M., Stern, M. and Stark, G. R. (1979) Efficient transfer of large DNA fragments from agarose gels to diazobenzyloxymethyl-paper and rapid hybridization by using dextran sulfate. Proc. Natl. Acad. Sci. USA 76:3683–3687.
34. Meinkoth. J. and Wahl, G. (1984) Hybridizatiois of nucleic acids immobilized on solid supports. Anal. Biochem. 138:267–284.
35. Reed. K. C. (1991) Nucleic acid hybridizations with positive charge-modified nvlon membrane. In "Methods in Gene Technology", Dale. J. W. and Sanders. P. G., eds. (JAI Press. London) 1:127–160.
36. Dyson, N. J. (1991) Immobilization of nucleic acids and hybridization analysis. In "Essential Molecular Biology: A Practical Approach", Brown, T. A., ed. (IRL Press at Oxford University Press, Oxford UK) 2:111–156.

37. Keeler, K. D., Mackenzie, N. M. and Dresser, D. W. (1983) Flow microfluorometric analysis of living spermatozoa stained with Hoechst 33342. J. Reprod. Fertil. 68:205–212.

38. Johnson, L. A. (1987) Separation of X and Y chromosome-bearing mammalian sperm by DNA content using flow cytometric analysis and sorting. Biol. Reprod. 36:80.

39. Simpson, J. L. and Elias, S., eds. (1994) "Fetal Cells in Maternal Blood: Prospects for Noninvasive Prenatal Diagnosis." (The New York Academy of Sciences, New York).

40. Wu, D. Y. and Wallace, R. B. (1989) The ligation amplification reaction (LAR): amplification of specific DNA sequences using sequential rounds of template-dependent ligation. Genomics 4:560–569.

41. Barany, F., Zebala, J., Nickerson, D., Kaiser, R. J., Jr. and Hood, L. (1996) Thermostable ligase-mediated DNA amplifications system for the detection of genetic disease. U.S. Pat. No. 5,494,810.

42. Mullis. K. B., Erlich. H. A., Arnheim, N., Horn, G. T., Saiki, R. K. and Scharf. S. J. (1987) Process for amplifying, detecting, and/or cloning nucleic acid sequences. U.S. Pat. No. 4.683,195.

43. Mullis, K. B. (1987) Process for amplifying nucleic acid sequences. U.S. Pat. No. 4,683,202.

44. Erlich, H. A., ed. (1989) "PCR Technology. Principles and Applications for DNA Amplification." (Stockton Press, New York).

45. Kwoh, D. Y., Davis, G. R., Whitfield, K. M., Chappelle, H. L., DiMichele, L. J. and Gingeras, T. R. (1989) Transcription-based amplification system and detection of amplified human immunodeficiency virus type 1 with a bead-based sandwich hybridization format. Proc. Natl. Acad. Sci. USA86:1173–1177.

46. Malek. L. T., Davey, C. Henderson, G. and Sooknanan, R. (1992) Enhanced nucleic acid amplification process. U.S. Pat. No. 5.130.238.

47. Birkenmever, L. G., Carrino, J. J., Dille, B. J., Hu, H.-Y., Kratochvil, J. D., Laffler, T. G., Marshall, R. L., Rinehardt, L. A. and Solomon, N. A. (1995) Amplification of target nucleic acids using gap filling ligase chain reaction. U.S. Pat. No. 5,427,930.

48. Backman, K. C., Carrino, J. J., Shimer, G. H. and Yocum, R. R. (1996) Ligase chain reaction with endonuclease IV correction and contamination control. U.S. Pat. No. 5,516, 663.

49. Sanger, F., Nicklen, S. and Coulson, A. R. (1977) DNA sequencing with chain-terminating inhibitors. Proc. Natl. Acad. Sci. USA 74:5463–5467.

50. Smith, L. M., Sanders, J. Z., Kaiser, R. J., Hughes, P., Dodd, C., Connell, C. R., Heiner, C., Kent, S. B. and Hood, L. E. (1986) Fluorescence detection in automated DNA sequence analysis. Nature 321:674–679.

51. Prober, J. M., Trainor, G. L., Dam, R. J., Hobbs, F. W., Robertson, C. W., Zagursky, R. J., Cocuzza, A. J., Jensen, M. A. and Baumeister, K. (1987) A system for rapid DNA sequencing with fluorescent chain-terminating dideoxynucleotides. Science 238:336–341.

52. McBride, L. J., Koepf, S. M., Gibbs, R. A., Salser, W., Mayrand, P. E., Hunkapiller, M. W. and Kronick, M. N. (1989) Automated DNA sequencing methods involving polymerase chain reaction. Clin. Chem. 35:2196–2201.

53. McCombie, W. R., Heiner, C., Kelley, J. M., Fitzgerald, M. G. and Gocayne, J. D. (1992) Rapid and reliable fluorescent cycle sequencing of double-stranded templates. DNA Seq. 2:289–296.

54. Michelmore, R. W., Paran, I. and Kesseli, R. V. (1991) Identification of markers linked to disease-resistance genes by bulked segregant analysis: a rapid method. to detect markers in specific genomic regions by using segregating populations. Proc. Natl. Acad. Sci. USA 88:9828–9832.

55. Bentley, S. and Bassam, B. J. (1996) A robust DNA amplification fingerprinting system applied to analysis of genetic variation within Fusarium oxysporum f.sp. cubense. J. Phytopathol. 144:207–213.

56. Bassam, B. J. and Bentley, S. (1995) Electrophoresis of polyester-backed polyacrylamide gels. BioTechniques 19:568–570.

57. Bassam, B. J., Caetano Anolles, G. and Gresshoff, P. M. (1991) Fast and sensitive silver staining of DNA in polyacrylamide gels. Anal. Biochem. 196:80–83.

58. Rand, K. N. (1997) Use of crystal violet in agarose gels for preparation of DNA fragments. Lorne Conf. "Organisation and Expression of the Genome" 19:P1.29.

59. Reed, K. C. and Matthaei, K. I. (1990) Rapid preparation of DNA dot blots from tissue samples, using hot alkaline lysis and filtration onto charge-modified nylon membrane. Nucl. Acids Res. 18:3093.

60. Jeffreys, A. J., Neumann, R. and Wilson, V. (1990) Repeat unit sequence variation in minisatellites: a novel source of DNA polymorphism for studying variation and mutation by single molecule analysis. Cell 60:473–485.

61. Sakagami, M., Ohshima, K., Mukoyama, H., Yasue, H. and Okada, N. (1994) A novel tRNA species as an origin of short interspersed repetitive elements (SINEs). Equine SINEs may have originated from tRNA$^{Ser}$. J. Molec. Biol. 239:731–735.

62. Shuber, A. P., Grondin, V. J. and Klinger, K. W. (1995) A simplified procedure for developing multiplex PCRs. Genome Res. 5:488–493.

63. Lin, Z., Cui, X. and Li, H. (1996) Multiplex genotype determination at a large number of gene loci. Proc. Natl. Acad. Sci. USA 93:2582–2587.

64. Lee, S. H. and Clark, J. B. (1997) High-yield method for isolation of 1 DNA. BioTechniques 23:598–600.

65. Southern, E. M. (1975) Detection of specific sequences among DNA fragments separated by gel electrophoresis. J. Molec. Biol. 98:503–517.

66. Gebauer, F. and Richter, J. D. (1996) Mouse cytoplasmic polyadenylation element binding protein: an evolutionarily conserved protein that interacts with the cytoplasmic polyadenylation elements of c-mos mRNA. Proc. Natl. Acad. Sci. USA 93:14602–14607.

67. Sassaman, D. M., Dombroski, B. A., Moran, J. V., Kimberland, M. L., Naas, T. P., DeBerardinis. R. J., Gabriel, A., Swergold, G. D. and Kazazian. H. H., Jr (1997) Many human L1 elements are capable of retrotransposition. Nature Genet. 16:37–43.

68. Scott. A. F., Schmeckpeper, B. J., Abdelrazik. M., Theisen Comey, C., O'Hara. B., Pratt Rossiter, J., Cooley, T., Heath, P., Smith, K. D. and Margolet, L. (1987) Origin of the human L1 elements: proposed progenitor genes deduced from a consensus DNA sequence. Genomics 1:113–125.

What is claimed is:

1. An isolated polynucleotide, the polynucleotide having a sequence as set out in any one of SEQ ID NOS: 1 to 4 or 8 to 11, or a sequence which hybridises thereto under high stringency, wherein the polynucleotide hybridises specifically to the equine Y chromosome.

2. An isolated polynucleotide, the polynucleotide having a sequence containing nucleotides 990–2497 of SEQ ID NO: 8, 421–1920 of SEQ ID NO. 9, 421–1930 of SEQ ID NO. 10. or 1502–2996 of SEQ ID NO. 11 or a sequence which hybridises thereto under high stringency, wherein the polynucleotide hybridises specifically to the equine Y chromosome.

3. An isolated polynucleotide as claimed in claim 1 in which the sequence shares at least 60% homology with a sequence shown in any one of SEQ ID NOS 1 to 4 or 8 to 11.

4. An isolated polynucleotide as claimed in claim 3 in which the sequence shares at least 80% homology with a sequence shown in any one of SEQ ID NOs 1 to 4 or 8 to 11.

5. An isolated polynucleotide as claimed in claim 1 which has a sequence as set out in SEQ ID NO: 3 or a sequence which hybridises thereto under high stringency.

6. A vector including a polynucleotide sequence as claimed in claim 1.

7. A host cell including a vector as claimed in claim 6.

8. An oligonucleotide probe or primer of at least 18 nucleotides that hybridizes specifically to the equine Y chromosome, the oligonucleotide having a sequence that hybridises to a polynucleotide as claimed in claim 1.

9. An oligonucleotide probe or primer as claimed in claim 8 which includes a sequence selected from:

AGCGGAGAAAGGAATCTCTGG, (SEQ ID NO: 12) or

TACCTAGCGCTTCGTCCTCTAT (SEQ ID NO: 13).

10. An oligonucleotide probe as claimed in claim 8 in which the probe is conjugated to a detectable label.

11. An oligonucleotide probe as claimed in claim 10 in which the label is selected from a radioisotope, an enzyme, biotin, a fluorescer or a chemiluminescer.

12. A method of determining the sex of a horse, an equine fetus, an equine embryo or an equine cell(s) which method includes analysing a biological sample derived from the horse, fetus, embryo or cell(s) for the presence of a polynucleotide sequence as set out in any one of SEQ ID NOS: 1 to 4 or 8 to 11, wherein the presence of the polynucleotide in multiple copy number is indicative that the biological sample is derived from a male.

13. A method according to claim 12 wherein the multiple copy number is greater than 5 copies in the haploid genome.

14. A method according to claim 12 in which the biological sample includes one or more sperm cells.

15. A method according to claim 12 in which the biological sample includes nucleated fetal cells.

16. A method according to claim 12 in which the analysis involves Southern blot hybridisation, dot blot hybridisation or in situ hybridisation.

17. A method according to claim 16 in which the analysis involves the use, as a probe in the Southern blot hybridization, dot blot hybridization or in situ hybridization, of an oligonucleotide probe that hybridizes specifically to the equine Y chromosome, the oligonucleotide having a sequence that hybridises to a polynucleotide having a sequence as set out in any one of SEQ ID NOS: 1 to 4 or 8 to 11, or a sequence which hybridises thereto under high stringency, wherein the polynucleotide hybridises specifically to the equine Y chromosome.

18. A method according to claim 12 in which the analysis involves the polymerase chain reaction or ligation amplification reaction.

19. A method according to claim 18 in which the analysis involves the use, as a primer in the polymerase chain reaction or ligation amplification reaction, of an oligonucleotide primer that hybridizes specifically to the equine Y chromosome, the oligonucleotide having a sequence that hybridises to a polynucleotide having a sequence as set out in any one of SEQ ID NOS: 1 to 4 or 8 to 11, or a sequence which hybridises thereto under high stringency, wherein the polynucleotide hybridises specifically to the equine Y chromosome.

20. A kit for sex determination of a horse, an equine fetus, an equine embryo, an equine cell or a population of equine cells, which includes a polynucleotide as claimed in claim 1 or an oligonucleotide probe or primer of at least 18 nucleotides that hybridizes specifically to the equine Y chromosome, the oligonucleotide having a sequence that hybridises to a polynucleotide having a sequence as set out in any one of SEQ ID NOS: 1 to 4 or 8 to 11, or a sequence which hybridises thereto under high stringency, wherein the polynucleotide hybridises specifically to the equine Y chromosome.

21. An isolated polynucleotide as claimed in claim 1, wherein the polynucleotide is less than 500 nucleotides in length.

22. An isolated polynucleotide as claimed in claim 2, wherein the polynucleotide is less than 500 nucleotides in length.

* * * * *

SEQUENCE LISTING

<160> NUMBER OF SEQ ID NOS: 29

<210> SEQ ID NO 1
<211> LENGTH: 432
<212> TYPE: DNA
<213> ORGANISM: Equus caballus

<400> SEQUENCE: 1

| ccagaacgga | gcaggccttt | ccaagttcga | ggagaaagtt | agaaacctac | aagaaatcca | 60 |
| gagaaagcaa | aactatccta | cctggaaagg | gggaggagtc | agacaggtct | gagatggctc | 120 |
| tgaaactctg | tgtacttgga | ggttgccagg | acaacttagg | tatctgaggt | tgtttatgac | 180 |
| atcacggtga | ccatgttccc | caagttggcc | gcatggttac | agtctgagaa | ttgccctggc | 240 |
| tggtctatta | aaggaagaca | tacccagaaa | tagctttgac | aaacagaagt | cgtgcacaga | 300 |
| aactagaaga | gatcaaacag | actctgatta | caggcataag | aaaggactcc | ttgccaagaa | 360 |
| gcgagaagag | agggacaagc | actgagagga | gaacattctc | atctgttcaa | gtctatgggg | 420 |
| attccgttct | gg | | | | | 432 |

<210> SEQ ID NO 2
<211> LENGTH: 600
<212> TYPE: DNA
<213> ORGANISM: Equus caballus

<400> SEQUENCE: 2

| caatcgggtc | cagaataacg | acatacagct | gtggggctg | aaagagatta | gagaacgtga | 60 |
| acttccaagg | attgaaaatc | acctcaaaag | tcttactgat | gctacagaag | ggtagaccat | 120 |
| tccaaataca | tgaagaggaa | cactaccaag | agaacccgat | ccgtgctaag | cccaggaacc | 180 |
| aacgtaaagc | gctagcgtcc | atgatgttcc | tactaatcac | cttcacgaat | aatccaaaca | 240 |
| ggcccacatc | ttcccaagat | caggatacag | gttggtccaa | agtaaaagt | cagggccggc | 300 |
| cctgtggggg | agaaggcaag | tgcccaggtt | ctgatgggtg | gcccagccct | cagtctttca | 360 |
| cagaacgggt | gcagatcaca | ttagcactga | tgggaaatag | agatctcatg | ggacggtgaa | 420 |
| gacagagggc | atacataagt | agcaattgtg | aaggtcggtt | atcaatacgc | cccagaaaat | 480 |
| caaccatgat | aatattccaa | tctatgaaag | catctgatac | acttccacaa | aggaagaagg | 540 |
| aaggaaatca | tgggacctgc | caaggtggac | ttggcagagt | gctaagagat | gacccgattg | 600 |

<210> SEQ ID NO 3
<211> LENGTH: 230
<212> TYPE: DNA
<213> ORGANISM: Equus caballus

<400> SEQUENCE: 3

| gtcgtagcgg | agaaaggaat | ctctggattc | catgcaatcc | cagtcaaagt | ggcagccata | 60 |
| tttgccggag | agatagaaga | gagaatccta | aagtgtctag | ccagcaacaa | gagcccctga | 120 |
| ataggccaag | gaatcctcag | gaaaacgaac | aaagcaggac | ggatcacact | ttctgatttc | 180 |
| aacatagagg | acgaagcgct | aggtaccgaa | acggaacagt | ccgctacgac | | 230 |

<210> SEQ ID NO 4
<211> LENGTH: 285
<212> TYPE: DNA
<213> ORGANISM: Equus caballus

<400> SEQUENCE: 4

-continued

```
aaccgcggca tcgactagtc tcttcattgt cctaatgaga tccttctgga ctttggatta      60
tgcttaaggc agaaggacac tgtaggtctg ataaggccca agtccggcct cgtgtttgca     120
aacaagtttc aagattgaat cagcatggcc tccccataga cttgaacaga tgacaatgtt     180
ctcctctcag tgcttgtccc tctcttctcg cttattgcca aggattcctt tcctatgcca     240
agaatcagag tctgtttgat ctcttgcagt ttctgtgccg cggtt                     285
```

<210> SEQ ID NO 5
<211> LENGTH: 230
<212> TYPE: DNA
<213> ORGANISM: Equus caballus

<400> SEQUENCE: 5

```
gtcgtagcgg agaaaggaat ctctggattc catgcaatcc cagtcaaagt ggcagccata      60
tttgccggag atagaagaga gaatcctaa agtgtctag ccagcaacaa gagcccctga      120
ataggccaag gaatcctcag gaaaacgaac aaagcaggac ggatcacact ttctgatttc     180
aacatagagg acgaagcgct aggtaccgaa acggaacagt ccgctacgac                230
```

<210> SEQ ID NO 6
<211> LENGTH: 217
<212> TYPE: DNA
<213> ORGANISM: Equus caballus

<400> SEQUENCE: 6

```
kcggagggag gaatgtatgt attgcatgca atcccagtca aagtggcagc catatttgcc      60
agagagatag aagagagaat cctaaagttt ctagccagca acaagagccc tgaataggc     120
caaggaatcc tcaggaaaac gaacaaagca ggacgtatca cactttctga tttcaaccta    180
aaggaccack cggtaggtac cgagacggat cgtccgc                              217
```

<210> SEQ ID NO 7
<211> LENGTH: 220
<212> TYPE: DNA
<213> ORGANISM: Equus caballus

<400> SEQUENCE: 7

```
gtagcggaga aaggaatctc tggattccat gcaatcccag tcaaagtggc agccatattt      60
gccagagaga tagaagagag aatcctaaag tttctagcca gcaacaagag ccctgaata     120
ggccaaggaa tcctcaggaa aacgaacaaa gcaggacgta tcacactttc tgatttcaac    180
atagaggacg aagcgctagg taccgaaacg gaacagtcgc                           220
```

<210> SEQ ID NO 8
<211> LENGTH: 4693
<212> TYPE: DNA
<213> ORGANISM: Equus caballus

<400> SEQUENCE: 8

```
gaattcatca aatttgccaa atttgtctcg gaaaagcatt gtgtccatga actggattgc      60
caggaccacc tcgaatttgg agtttctgat ctcaggatgt caaagcaacc cagatgacca    120
cgggtactca gtgcttcgtt tgacctaggc taggatagca agagcacaa cgagtgacag     180
gtgcaaattc aaaaacagca accaagattc acgaaagcac tcacacctcg gcctagagaa    240
catacggtga ttcaagaaac acaaaattac tccctgggtg tgaaggagaa tggactgata    300
agcacatcaa agggagatag ctgagaagac catgacgagt atactgtgga aagaaaaaa     360
```

```
agggtccagg aaattgcaag gcgaacagat atcacacctg aataatccac gatgaaagat    420
gtcagttttt agacaggctc tgctagaacg attgaaagtc agagaaagcc acaagccaaa    480
aaacggcagc ggaggtcaaa cctgggctca ctgggaagtg tgagctatga cagagctcga    540
agcgggctct gaagcccttt gtccatgacg attgccagga cagcagacac acacttatga    600
ccaatcctct gacgtcacag tggcccccgac aaacaacctg gcatcctcta cacagtgcca    660
gagttgggct caagcagcat attcaatacc cattgcgctc aagtgcaggt tgccaatgga    720
acatgaaagg ggccggccgg tggtgcagcg gtgaggtccg cagcttctga gtcagtggcc    780
aggggtgggc cgcgtggaat cctctggggtg agcctcctca ccactgcttc agtcattctg    840
ggccaggagt ccaaggggggt gtagaggcag atgggaaggg acgttagata gggccagact    900
ttaacagcaa atacaagagc attgccagca gatgtgagca tagcgatgca cttctgccaa    960
aacacaacca attacaagtt gcaaagaata gaaaaaggga agctaaaaac aaacaaagaa    1020
acgaaaaaca cagcttgcca gtaccatgaa gaagatctct atgaagaacc ttagcaaaac    1080
aggtgaaagc tatgtcaatc gaaaccagc aaacctttgg ggagagaaat tcaagaagac    1140
aaaaggaaaa agaaggatat tttcagacct acgtatctaa gaattaacac actggagacg    1200
tccatagcgg agaaaggaat ttctggattc catgcaatcc cagtcaaagt ggcagccata    1260
tttgccagag agatagaaga gasaatccta aagtttctar ccagyracaa gagcccctga    1320
ataggccaag gaatcctcag gaaaaygaac aaagcaggac gtatcacact ttctgakttc    1380
aacatagagg acgaagcgct aggtaccgaa acggmacagt cgcgggctcc aaaacaggca    1440
cacagaccca tgcaacagaa tcgagagagc agagactaac tcaaatatac atggacagcc    1500
catttgcgac cagggagcca agaggacaca gtggaccaag gattgtctct ccaataaact    1560
gtgctgggaa gcctgcatag ccacaggaac acaacgagag tagaccatga tgttccacct    1620
ggcaaaggca ccacctgaaa aagattaaag ccctgaatgg cacacttgaa accgtgaaac    1680
ttttaggaga agacctaggc agagtgctct ttgccatctg tctgagccgc ctatttggaa    1740
gaagcctgtc tgcagggca agggcagcaa aggagacaag aaacaaacgg gaccacctca    1800
aatgcagacg cttctgccca gtcaaggaaa ccatcgactc actgcaaaga cagcacaaca    1860
cctgggagtg gatgtttgca aagcacacat cggacgaggg gtgaaaagcc cacagatgca    1920
atcaactcac acgtctccac aagaaaaaaa acaagcaaat gaaaacctgg caaaagatg    1980
gatacagaga tttctcccaa taagatctaa agagggccaa caggttcatg aaaacttgtt    2040
cacccgcatt aagtcttagt ccaatgcaaa tccaaaccgc aatgacatag cagctcactg    2100
tggtcagaat ggctataagg aggcccacag gaaaacaaca agtgtcagag aggaggtgga    2160
gagaagggaa gcctcctgca ctgctggtgg cagtgtaaac gggtgcagcc actaggccaa    2220
gcggtgtgga actgcctcag aaatttaaga acccatgtcc cataggatcc agctattcct    2280
cggggccgtg tttagacaaa gaactcggaa acacaaccgc taaagacatg tgcaccgctg    2340
agttcaccac agccttattc ccgctctcca agacttggaa gccgcctggt gccgagcaag    2400
ggacgaatag agaaggacat gggctatagc cacacatggc ataccactca gcgggaacaa    2460
aggatgcaat ccagccattt gtgaccacca gaatggctgg gagggtttca gggtaagtga    2520
aaaaggcccc aggacatag tcaaataccg tagcatcaca cttacaagga gaagataaaa    2580
aaagcactaa ccaacaggtg gcgcaggaca tttgattggg ggtgcccaga ggcaaagcgg    2640
ggcggtggcg agggtgtaag agatgatgag gcacaagtgt gtggtgaggt catgtgattc    2700
ggcttaagct ggtgaagagg atgtcaacta cacggaagtc caaatcgatg aggatgcaaa    2760
```

```
tctgaaagac ataggatatt gtaacgcagg gttaaggcaa taaattcacc tacaatcaaa    2820
aatcccaaac gtgggtccag aatgacgaca tacagctctg ggagctaaaa gagattagag    2880
aaattgaaca tccaaggatg gaaaatcacc tcaaaaggct tactgatgct acagaagggt    2940
agacccattc caaatccatg aagaagaatg cttaccaaga gaccttgatc cgtggttaag    3000
cccttggacc aaacccaaaa cattaccgtc catgatgtta ctacttaata accttcacaa    3060
atcatccaaa caggcccaca tcttcccaag ttcaggccac aggttggtcc aaaagtacaa    3120
gtcagggccg gccctgtggt ggagtgggca agtgccctcg ttccgcttgg gtggcccggg    3180
cctcactctt tcacagcccg ggtgcagatc acattagcac tgttaggaaa tagagatttc    3240
atgggacggt gcgacagag gtcataaaga agtagcaatt gtgagggtcc attatcagca     3300
cgccacagaa aaacaaccat gggaatatta caatctatga aggcatctgg tacacttccc    3360
caaaggaaga aggaaggaaa acatgggacc tgccaaggtg gacttggcag agtgctagga    3420
gatgacacga tcattgcgca tcagaggatt gcctgggcaa cttcaacttg ggagggagtc    3480
caggactttc tctggggaag gtccagtcac ttggccctct ccccaagaca taagatataa    3540
gagccagggt aatcttacag ggaagaaacc agtgtctaga gtgaacggag caggcctttc    3600
caagttcgag gagaaagtta gaaaccgaca agaaaatcag aaaaaggtaa actatcctac    3660
ctggaaaggg ggaggagtca gactggtctg agatggcact gaaactctgt gtgcttggag    3720
gttgtcagga caacttagcc ttctgaggtt ctttatgaca tcagggcgaa catgtccccc    3780
aagatggccg catggttaca gtctgagtat tggcctaggc tgggctacta aaggatgaca    3840
tacccagaaa cagctttgac aaagagaaag cgggtacaga aactggaaga gatcaaacag    3900
actctgattc caggcataag aaagaaatcc ttggcaagaa gcgagaagag agggacaagc    3960
actgagagga gaacatcgtc atctattcaa gtctagggga ggccatgctg atgcaagcct    4020
gaaacttgat tggaaacacg aggtcggact tgggccttat cagacctaca gtgtccttct    4080
gccttaagca taatccaaag tcacgaagga tctcttgagg acattgaata ggagagtcga    4140
tgcctccttt cctaggcccc tagcattctt tgaagatcag tctcactttc cataactctg    4200
gcgtcacggg ggcccactgg atacatgcta atgcgtccca agaaatgtct tggaagcctt    4260
aaatgaatgg agccctgtca tgcttggggt aggtctcttt gttgggaacg gcctctccaa    4320
gtgtgctgaa aatcacccct ttccagaggg cttggttcct ttgtgaaggc tgccctctca    4380
ggcttgtgtg ctcactttgg ctccaatgaa attctctccc cctacctctt cccgtatatg    4440
gattactgat tacgtgcttt gacgccatat ggaattaagc tggctgaaaa ttagaacatt    4500
acaattctgt ttccagaaat atagacatgc cagggctgag gctgtaggtc aaacaaatgg    4560
cacacactat agacataaag taagcccgta actagacgga atctagggca acgttcaact    4620 gtcagggca agttcgaacc tttccaaatc cacaaaaaag acagaaaaat atcattcctg     4680
gagagtggaa ttc                                                       4693
```

<210> SEQ ID NO 9
<211> LENGTH: 3430
<212> TYPE: DNA
<213> ORGANISM: Equus caballus
<220> FEATURE:
<221> NAME/KEY: unsure
<222> LOCATION: (1110)
<223> OTHER INFORMATION: n at position 1110 = a, t, c, or g
<221> NAME/KEY: unsure
<222> LOCATION: (1656)
<223> OTHER INFORMATION: n at position 1656 = a, t, c, or g
<221> NAME/KEY: unsure
<222> LOCATION: (1658)
<223> OTHER INFORMATION: n at position 1658 = a, t, c, or g
<221> NAME/KEY: unsure
<222> LOCATION: (1995)
<223> OTHER INFORMATION: n at position 1995 = a, t, c, or g
<221> NAME/KEY: unsure
<222> LOCATION: (2087)
<223> OTHER INFORMATION: n at position 2087 = a, t, c, or g
<221> NAME/KEY: unsure
<222> LOCATION: (2781)
<223> OTHER INFORMATION: n at position 2781 = a, t, c, or g

<400> SEQUENCE: 9

```
aagcttgccg ggacagcaga cacacaatta tgaccaatcc tctgacgtca cagtggcccc      60
gacaaacaac ctggcctcct ctacactgtg ccagagttgg gctcaagcag catattccag     120
ccacactgcg ctcaactgca ggtttccaat agaacatgaa agaggccgcc ggtggtgcag     180
cggtgaggtc cgcagctttg tgtcggtggc ccgtggtggg ccagtggaa  tcctggggtt     240 gagcctcctc accactgctt cagtcattct ggggcaggcg tccgagggcg tgtagaggct     300
gatgggaagg gacgttagat agggccagaa ttccacagca aatacaggag cattgccggc     360
agacgtgagc acatcgatgc acttctgcca aaacagaacc aataacaagt tgcaaagaac     420
agaaaaacgg aagctaaaca aataaacaaa aataaacaca gcttcccagt acgaagaaga     480
agatgtctat gaagaacctt agcaaaacag gtgaaagcta tgttaatcga aaatagcaaa     540
tgtttgggga gagaaattta agaagacaca aggaaaaaga aggatattcc gcgacctagg     600
aatggaagaa ttaacacact ggaaacgtcc atagcagaga aaggaatctc tggattccag     660
gcaatcccag ttaaagtgga agccttcttt gccagarata tagaagagag aatcctaaag     720
tttctagcca gcaagaagag cccctgaata ggccaaggaa tcctcaggaa acgaacaaa     780 gcaggacgta tcacactttc tgatttcaac atagagcacg aagcgctagg tactgaaacg     840
gtacagtcca gtcccaaaaa caggcacaca gacaaatgta acactataga gagcccagag     900
cccaactcaa acatacatgg acagcccatt tgcgaccagg gagccaagag gacacagtgg     960
acaaacgaga gtctctccaa aaaacggtgc tgggaagcct gcacagccac atggtacaca    1020
acgagagtag accatgatgt tccacctggc acacgcacca tctgaaattg attcaagccc    1080
tgaatggcgc acttgaaacc cgggaacttn ttaggagaag acctaggcag agcgctctkk    1140
cccatctgtc tgagccgccc acttggaaga agcctgtctg actcggcaag ggcagcaaag    1200
gagacaagaa gcaaacggga ccacctcaaa tgcagacgct tctgcccagt caaggaaacc    1260
atcgactcaa ggcaaagaca gcacaacaac tgggagtgga tgtttgcaaa gcacacatcg    1320 gacgagggt  gaaaagccca agatacaat  caaatcacac gtctccacaa gaaataaaac    1380
aagccaatga aaacctgcgc aaaagatgga cacagagact tctcccaaga agatctaaag    1440
agggccaaca ggtgcatgaa aacttgttca ccctcattaa gtctgaggcc aatgcaaatc    1500
caaaccgcaa tgacatagca gctaactgag ttcagaatgg ctataaggag accgacagga    1560
cagcaacaat tgtcagaggg gaggtggaga aagggaagc  ctcctgcact gctggtggca    1620
gtgtaaatgg gtgcagccac taaggcaagc aatgtngnac tggccacaga aatttaagaa    1680
tccatgtcct ttaggatcca gcgattcctc ggggcgtgt  ttagcaaag  aaatcggaaa    1740 ctcaacccgc taaagacatg tgcatcgctg agttcaccac agcttactcc gctctccaag    1800
acttggaagc gcctggtgc  ccaacaagga agaatggaga agaacatggc tatagccaca    1860
caatggcata ccactcattg cggaccagat gccatccagc cattgtggcc accagatggt    1920
```

-continued

```
tgaggtttag gtgaagtgaa caggcccagg aaatagtgaa ttccatagca cgtcacttac      1980
aaggagaaga aaaancaagc actaacccaa caggtggccc ttggacaatt tgattggggg      2040
tgcccaaagg caaaaaaggg ccgttttgga aggagaaagg gatgatnagg cacaagtgcg      2100
tggtgagtgc ctgtgattcg gcttacgctg gagaagagga tgtcgcctac acggaagtct      2160
aaatcgatgg ggatgtaaat ctgaaagaca tcggatattc taatgcaggg ttatggtaat      2220
aaattcacct acaatgaaaa atccaaaaag gggtccggaa tgacggcata cagctctggg      2280
ggctgaaaga gattagagaa ggcgaacttt caaagatgga aaatcacctc aaaaggctta      2340
ctgatgctac agaagggtag agcattccaa atacatgaag gggaatacta ccatgagaac      2400
cttatccatg cttagcccag gaacccacgg aaaacgttac cgtccatgat gttactacta      2460
atcaccttca cgaataatcc aaacaggccc acatcttccc aagttcaggc cacgggtcgt      2520
ccaaaagtac aagtcaggga cggcgctgcg gggagcgggc aaatgcccat gttccgcttg      2580
gtggcccggg cctcactctt tcacagcacg ggtgcagatc acattagcac tgttaggaaa      2640
tagagatttc atggacrctc ggacaaaggk yataaatagg tagcaattgt gaagggtcag      2700
ttatcaatac gccccagaaa agccaaccat gagaatattc caatctatga aggcatctgg      2760
gtcactttcc acaaaggaag naggaagaaa acatgggacc tgccaaggtg gacttggaag      2820
agtgctagga gatgacacgg taattgggca tcagaggact gcctgggcaa ttcaacttgg      2880
aagggagtcc aggactttct gtggggaagg tccagccact tggccctttc cccaagacta      2940
aagagataag agccagggtt atcttacagg gaagaaacca gtgtctagag agaatggagc      3000
aggcctttcc aagttcgagg agaattttag aaacttacaa gaaataaaga aaaaggaaaa      3060
caatcctacc tggaaagggg gaggagtcag actggtctga gatggctctg gaactctgtg      3120
tgcttggagg ttgtcaggac aacttagcct tctgaggttg tttatgacat cacggtgaac      3180
atgtccccca agatggccgc atggttatag tctgaggatt ggcctaggct gggctattaa      3240
agggagacat acccaaaaac agctttgaca aacagaaagc gggcacagaa actggaagag      3300
atcaaacaga ctctgattcc aggcataaga aaggaatcct tggcaagaag cgagaagaga      3360
gggacaagca ctgagaggag aacattgtca tctgttcaag tctatgggga ggccatgctg      3420
attcaagctt                                                             3430
```

<210> SEQ ID NO 10
<211> LENGTH: 3450
<212> TYPE: DNA
<213> ORGANISM: Equus caballus
<220> FEATURE:
<221> NAME/KEY: unsure
<222> LOCATION: (2122)..(2341)
<223> OTHER INFORMATION: n at positions 2122 through 2341 = a, t, c, or g
<221> NAME/KEY: unsure
<222> LOCATION: (2345)
<223> OTHER INFORMATION: n at position 2345 = a, t, c, or g

<400> SEQUENCE: 10

```
aagcttgccg ggacagcaga cacacaatta tgaccaatcc tctgatgtca cagtggcccc        60
gacaaacaac ctggcctcat ctacacagtg cgagagttgg gctcaagcag catattcaag       120
tcccattgcg ttcaactgca ggttgccaat ggaacatgaa acggccggcc ggtggtgcag       180
cggtgaggtc cgcagattct gggtcggtgg acaggggtgg gccgggtgga atcctggggg       240
tgaggctcct caccactgct tcagtcattc cgggcaggc gtccgcgtgg ttgtagaggc       300
agatgggaag ggacgttaca tagggccaga cgtccacatc aaatacagga gcattgccag       360
```

```
cagatgtgag aacagcgatg cacttctgcc aaaacacaac caattacaag ttgaaaagat    420
tagaaaaacg gatgctaaaa acaaacaaac aaacaaaaaa cacagcttgc cagtacgaag    480
aagaagatct ctatgaagac acttagcaaa acaggtgaaa gctatgtcaa tagaaaacca    540
gcaaacgttt ggggaaagaa attcaagaag acacaaggaa aagaaggat ataccgggac     600 ctaggaatgg aagaattaac acactggaaa cgaccatagc ggagaaggga atatctggat    660
tccattcaat cccagtcaaa gtggcagcca tcttcgtcag agagatagaa gagagaatcc    720
taaagtttct agccagcaat aagagcccct gaataggcca aggaatcctc aggaaagcaa    780
acaaagcaga acgtatcaca ctttctgatt tcaacataga ggacgaagcg ctaggtaccg    840
acacggcaca gtccgggccc aaacacagac acacagaccc atgcaacaga atcgagagcc    900
cagagcccaa ctcaaacata catggacggc ccatttgcga ccaaggagcc aagaggagac    960
agcggacaaa ggagagtctc tccaataaac gctgctggga agtctgaaca gcccacatgt   1020
gcacaacgag agtagaccat gatgttccac ctggcacacg cagaacctga aatggattaa   1080
agccctgaat ggcacacttg aaaccgtgaa acttgtagga gaagacctag gcagagtgct   1140
ctttgccatc tgtctgagcc acctatttgg aagaagcctg tctgactggg caagggcagc   1200
aaaggagaca gaaacaaac gggaccacct caaatgcaga cgcttctgcc cagtcaagga    1260
aaccatcgac tcaatgcaaa gacagcacaa caactgggag tggatgtttg caaagcacac   1320
atcggactaa gggtgaaaag cccaaagata caatcaactc acacgtctcc acaagaaaaa   1380
aaacaagcca atgaaaacct gggcaaaaga tggacacaga gatttctccc aagaagatct   1440
aaagagggcc aacaggtgca tgaaaacttg ttcaccctca ttaagtctga ggccaatgca   1500
aatccaaacc gcaatgacat agcagctcac tgtggtcaga atggctataa ggagtccgac   1560
aggaaaacaa ttgtcagaga ggaggtggag agaagggaag ccgcctgcac tgctggtggc   1620
actgtaaacc ggtgcagcca ctatgccaag cggtgtggaa ctgcctcagg aatttaagaa   1680
tccatgtccc ataggatgcc gctattcctc gggggcgtgt ttagccaaag aactcggaaa   1740
cacaaccgcc taaagacatg tgcaccgctg agttccccac agccttactc ccgctctcca   1800
agacttggaa gccacccctgg tccccagcaa gggacgaatg gagaaggaac atgggctata   1860
gccacacaat ggcaaaccac tcagcgggaa caaaggatgc aatccagcca tttgtgagca   1920
ccagaatggc tgggaggctt ttaggggaag tgaaacaggc cccagggaca tagtcaaata   1980
ccgtaggatc tcactttcaa ggagaagata aagaagaac taaccaacag gtggcgctgg   2040
acatttgatt gggggtgccc agaggcaaag cggggccatg ggggaggagt gacagagata   2100
gatgaggcaa atgggtgtga cnnnnnnnnn nnnnnnnnnn nnnnnnnnnn nnnnnnnnnn   2160
nnnnnnnnnn nnnnnnnnnn nnnnnnnnnn nnnnnnnnnn nnnnnnnnnn nnnnnnnnnn   2220
nnnnnnnnnn nnnnnnnnnn nnnnnnnnnn nnnnnnnnnn nnnnnnnnnn nnnnnnnnnn   2280
nnnnnnnnnn nnnnnnnnnn nnnnnnnnnn nnnnnnnnnn nnnnnnnnnn nnnnnnnnnn   2340
nyacntcaaa aggcttactg atgcgacaga agggtagcca ttccaaatac atgtagagga   2400
atactaccaa gagaacctga tccatgctaa acccaggaac caacggaaaa tgttaccgtc   2460
catgatgttg ctactaatca ccttcaggaa taatccaaac aggccacaa cttccccaag    2520 ttcaggccac aggttggtcc aaagtcaagt ccagtttcgg ccctgtggtg gatcgggcaa   2580
gtgaccacgt tccgcttggg tggcccgggc ctcactcttt cacagcacgg gtgcagatca   2640
cattagcact gtaaggaaat agagatttca tgggacggtg cggacagagg tcataaagaa   2700
gtagcaattg tgagggtccg ttatcaatac accccagaaa agcatccatt agaatattcc   2760
```

| | |
|---|---|
| aatctatgaa ggcatctggt acacttcccc aaaggaagaa ggaaggaaaa catgggacct | 2820 |
| gccaaggtgg acttggcaga gtgctaggag atgacaggat cattgggcat ctgaggatta | 2880 |
| cctgggcaac ttcaacttgg gatggagtcc aggactttct ctggggaagg tccagccact | 2940 |
| tggccctctc cccaagacat aagagataag agccagggta atcttacagg gaagaaacca | 3000 |
| gtgtctagag agaatggagc aggccattcc aagttcgagg agaaagttag aaaccgacaa | 3060 |
| gaaatccaga aaaaggaaaa ctatcctacc tggaaagggg gatgagtcag actggtctga | 3120 |
| gatggctctg aaactctgtg tgcttggagg ttgtcaggac aacttagccg tctgaggttg | 3180 |
| tttgtgacat cacggtgaac atgtccccca agatggaggc atggttacag tctgagcatt | 3240 |
| ggcctagcct gggctattca aggggacata acccaaaaac agctttgaca acagaaagc | 3300 |
| gggcacagaa actggatgag atcaaacaga ctctgattcc aggcataaga agggaatcct | 3360 |
| tggcaagaag cgagaagaga gggtcaagca ctgacaggag aacatttccc tctgttcaag | 3420 |
| actataggga ggccatgctg attcaagctt | 3450 |

<210> SEQ ID NO 11
<211> LENGTH: 4344
<212> TYPE: DNA
<213> ORGANISM: Equus caballus

<400> SEQUENCE: 11

| | |
|---|---|
| aagcttgaat cagcatggcc tccccataga cttgaacaga tgacagtgtt ctcctctcag | 60 |
| tgcttgtccc tctcttctcg cttcttgcca aggattcctt tcttatgcct ggaatcagag | 120 |
| tctgcctgat ctcctccagt ttctgtgccc gctttctgtt tgtcaaagct gtttctgggt | 180 |
| atgtctccct ttaatagccc agcctaggcc aatcctcaga ctgtaaccat gcggccatct | 240 |
| tgggggacat gttcaccgtg atgtcataaa caacctcaga aggctaagtt gtcctgacaa | 300 |
| cctccaagca cacagagttt cagagccatc tcagaccagt ctgactcctc ctcctttcca | 360 |
| ggtgattact agtaacatca tggagggtag cctttcagtt tgttcctgga cttagcactg | 420 |
| atcaggttct cttttgtagta ttcctcttca tgtatctgga atggtgtacc cttctgtcgc | 480 |
| atcagtaaga ctttttcaggt gattttctgg tacacttccc caaagcaaga aggaaggaga | 540 |
| acttgggacc tgccaaggtg gtcttggcag agtgctagga gatgagaaca aaggatgcaa | 600 |
| tccagccatt tgtgaccatc agaatgggtg ggagggtttt aggggaagtg aaacaggccc | 660 |
| cagggacata gtcaaacacc ataggattca cttcaagga gaagatataa gaagcactaa | 720 |
| ccaacaggtg gcgctggaca tttgattggg ggtgcccaga ggcaaagccg ggcagtgggg | 780 |
| gagggtgaaa gagatgatga ggcacaagtg tgtggtgagg gcctatgatt cggcttacgc | 840 |
| tggggaagag gatgtcacct acacggaagt ctaaatcgat gaggatgtaa atctgagaga | 900 |
| cataggatgt tctaatgcag ggttatggca ataaattcac ctacaatcaa aaatccaaaa | 960 |
| agtggtccag aatgactcca taaagctctg ggggctgaaa gagattagag acggtgaact | 1020 |
| tcaaaggatg gaaaatcacc tcaaaagtct tagtgatgcg acagaagggt agaccattcc | 1080 |
| aaatacatga agaggaatac tacaaagaga acctgatccg tgctaagccc aggaaccaac | 1140 |
| ggaaaatgtt accgtccatg atgttactac taatcacctt catgaataat ccaaacaggc | 1200 |
| cctcatcttc ccaagatcag gccacaggtt ggtccaaaag tacaagtcag ttccggctct | 1260 |
| gtggtggagc gggcaagtgc ccacgttccg cttgggtggg cagggcttca gtcttttcaca | 1320 |
| gcacgggtca gatcccatta gccttgttag gaaatagaga tttcttggac ggtcggacag | 1380 |

```
aggtcataaa gggacgttag ataaggcaga tttccacagc aaatacagga gcattcccag   1440
cagatgtgat cacaacgatg cacttctgcc aaaacacaac cacttacaag ttgcaaagat   1500
tagaaaaccg gaagctaaaa acaaaaaaac aaaaacaaaa cacagcttgc cactacgaag   1560
aagaagatct ctatgaagaa ccttagcaaa acaggtgaaa ggtatgtcaa tctaaaacca   1620
acaaacgttt ggggaaagaa attcaagaag acacaaggaa taagaaggat attccgggac   1680
ctaggaatgg aagaattagc cacttgaaaa cgtccataga ggagaaagga atctctggat   1740
tccatgcaat cccagtcaaa gtggcagcca tatttgccag agagatagaa gagagaatcc   1800
taaagtttct agccagcaag aaaagcccct gaataggcca aggaatcctc aagaaaacga   1860
acaaagcagg acgatcaca ctttctgatt tcaacataga ggacgaagcg ctaggtactg   1920
aaacggcaca gtccgggccc aaaaacaggc acacagaccc atgcgacaga atcgagagcc   1980
cacagcccaa ctcaaacata catggacacc ccatttgcga ccaggagcc aagaggagac   2040 agtggacaaa ggagagtctc tccaataaac gggctgggaa gcctgacagc cacatagaac   2100
acaagaatag accatgatgt tccacctggc agacgcccac tgaatggatt caagccctga   2160
tggccacttg aaccgtgaac ttgtaggaga agacctagca gagtgctctt tgccatctgt   2220
ctgacccgcc tatttggaag caggctgtct gactgggcaa gggcagcaaa ggagacaaga   2280
aacaaacggg accacctgaa atgcagacgc ttctgcccag tcaaggaaac catcgactca   2340
atgcaaagac agcacaacac ctgggagtgg atgttagcaa agcacacatc ggatgagggg   2400
cgaaaagccc aaagatacaa tcaactcaca cgtctccaca agaaaaaaaa caagccaatg   2460
aaaatctggg caaagatgg acacagagat ttctcccaag aagatctaag agggccaaca   2520
ggtgcatgaa aacttgttca ccctcattag tctaaggcca atgcaatcca accgcaatga   2580
catagcagct cacttgtggt cagaatggct ataaggaggc agacaggaaa acaacaagtg   2640
tcagagagga ggtggagagt aggaagcctc ctgcactgct ggtggcagtg taaacgggtg   2700
cagccagtag gccaagcggt gtgaaactac ctcagcaatt tcagaatccg tgtaccatag   2760
gatccagcta ttcctcgggg gcgtgtttag ccaaaaaact cggaaacaca aactcctaaa   2820
gacatgtgca ccgctgagtt caccacagcc ttactcccgc tctccaagac ttggaagccg   2880
tcctggtgcc gagcaaggga cgaatgtaga aggaacatgg gctatagcca cacaatggca   2940
taccagtcag tgggaacaaa ggttgcaatc cagtcatttg cgaccaccag aatggcttgg   3000
agagttttat gggaagtgaa acaggaccca gggatatagt caaataccgt agcataacac   3060
ttacaaggag aagataaaaa agcactaac caacaggtgg cgctggacat ttgattgggg   3120
gtgcccagag gcaaagcggg gcggtggggg aggtttaaag acttgatgag gcacaagtgt   3180
gtggtgagga catgtgattc ggcttatgct ggtgaagagg atgtcaccta cacggaagac   3240
taaatcgatg agcatgtaaa tgtgaaagac ataggtgtt ctaatgcaag gttatggcac   3300
taaattcacc tacaatcaaa aatccaaaaa ggggtccaga atgacggcat acagctctgc   3360
gggctgaaag agattagaga aggtgaactt ccaaggatgg aaaatcacct caaaaggctt   3420
actgatgcta cagaagggtg accattccaa atacttgaag aggaatacta ccaagagaac   3480
ctgatcagtg ctaagcccag gaaccaacgg aaaacgttac catccatgat gttactacta   3540
atcaccttcg cgaataatcc aaacaggccc acatcttccc aagttcaggc cacatgttgg   3600
tccaaaagta caagtcaggg aagccctgtg ggggagcggg caaggccaa cgttccgctt   3660 gggtggccag ggcctcactc tttcacagca cgggtgcaga tcacattagc actgttagga   3720
aatagagatt tcatgggacg gtgcggacag aggacataaa gaagtagcaa ttgtgagggt   3780
```

```
cctttatcaa tacgccccaa aaaagcaacc atgacagtat tccaatctat gaaggcatct    3840
ggaacacttc cccaaaggaa gaaggaagga atcatgggga cctgccaaga tggacttggc    3900
agagtgctag gagatgactg gatcattgca catcagagga ttgcctgggc aacatcaact    3960
tgggagggag tccaggactt tctctgggga aggtccagcc acttatccct ctctccaaga    4020
cataagagca agagccaggg tatcttacag ggaagaacca gtgtctagag agaatggaca    4080
accctttcca agttcgagga taaagttcga aaccgacaag aaatccagaa aaaggaaaac    4140
tatcctacct ggaaaggggg aggagtcaga ctggtctgag atggctctga aactctgtgt    4200
gctgggaggt tgtcaggaca acttagactt ctgaggttgt ttatgacata acggcgaaca    4260
tgtcccccaa gatggccgca tggttactgt gtgaggattg gcctaggctg ggctattaaa    4320
ctgagacata cccagaaaaa gctt                                           4344

<210> SEQ ID NO 12
<211> LENGTH: 21
<212> TYPE: DNA
<213> ORGANISM: Equus caballus

<400> SEQUENCE: 12
agcggagaaa ggaatctctg g                                                21

<210> SEQ ID NO 13
<211> LENGTH: 22
<212> TYPE: DNA
<213> ORGANISM: Equus caballus

<400> SEQUENCE: 13
tacctagcgc ttcgtcctct at                                               22

<210> SEQ ID NO 14
<211> LENGTH: 23
<212> TYPE: DNA
<213> ORGANISM: Equus caballus

<400> SEQUENCE: 14
ttcgtcctct atgttgaaat cag                                              23

<210> SEQ ID NO 15
<211> LENGTH: 21
<212> TYPE: DNA
<213> ORGANISM: Equus caballus

<400> SEQUENCE: 15
gtcgtagcgg agaaaggaat c                                                21

<210> SEQ ID NO 16
<211> LENGTH: 20
<212> TYPE: DNA
<213> ORGANISM: Equus caballus

<400> SEQUENCE: 16
agcggactgt tccgtttcgg                                                  20

<210> SEQ ID NO 17
<211> LENGTH: 21
<212> TYPE: DNA
<213> ORGANISM: Equus caballus

<400> SEQUENCE: 17
```

```
gcccagtgtt tcgttggttc g                                          21

<210> SEQ ID NO 18
<211> LENGTH: 25
<212> TYPE: DNA
<213> ORGANISM: Equus caballus

<400> SEQUENCE: 18
catagttgta tattcttcgt tgtgg                                      25

<210> SEQ ID NO 19
<211> LENGTH: 41
<212> TYPE: DNA
<213> ORGANISM: Equus caballus

<400> SEQUENCE: 19
gcggtcccaa aagggtcagt agcggagaaa ggaatctctg g                    41

<210> SEQ ID NO 20
<211> LENGTH: 42
<212> TYPE: DNA
<213> ORGANISM: Equus caballus

<400> SEQUENCE: 20
gcggtcccaa aagggtcagt tacctagcgc ttcgtcctct at                   42

<210> SEQ ID NO 21
<211> LENGTH: 41
<212> TYPE: DNA
<213> ORGANISM: Equus caballus

<400> SEQUENCE: 21
gcggtcccaa aagggtcagt gcccagtgtt tcgttggttc g                    41

<210> SEQ ID NO 22
<211> LENGTH: 45
<212> TYPE: DNA
<213> ORGANISM: Equus caballus

<400> SEQUENCE: 22
gcggtcccaa aagggtcagt catagttgta tattcttcgt tgtgg                45

<210> SEQ ID NO 23
<211> LENGTH: 10
<212> TYPE: DNA
<213> ORGANISM: Equus caballus

<400> SEQUENCE: 23
ccagaacgga                                                       10

<210> SEQ ID NO 24
<211> LENGTH: 10
<212> TYPE: DNA
<213> ORGANISM: Equus caballus

<400> SEQUENCE: 24
caatcgggtc                                                       10

<210> SEQ ID NO 25
<211> LENGTH: 10
<212> TYPE: DNA
<213> ORGANISM: Equus caballus

<400> SEQUENCE: 25
```

```
gtcgtagcgg                                                          10

<210> SEQ ID NO 26
<211> LENGTH: 10
<212> TYPE: DNA
<213> ORGANISM: Equus caballus

<400> SEQUENCE: 26
tcacgtacgg                                                          10

<210> SEQ ID NO 27
<211> LENGTH: 10
<212> TYPE: DNA
<213> ORGANISM: Equus caballus

<400> SEQUENCE: 27
aaccgcggca                                                          10

<210> SEQ ID NO 28
<211> LENGTH: 23
<212> TYPE: DNA
<213> ORGANISM: Equus caballus

<400> SEQUENCE: 28
atttaggtga cactatagaa tac                                           23

<210> SEQ ID NO 29
<211> LENGTH: 23
<212> TYPE: DNA
<213> ORGANISM: Equus caballus

<400> SEQUENCE: 29
attatgctga gtgatatccc gct                                           23
```